(12) United States Patent
Lindsay et al.

(10) Patent No.: US 10,422,787 B2
(45) Date of Patent: *Sep. 24, 2019

(54) SYSTEM AND METHOD FOR SINGLE MOLECULE DETECTION

(71) Applicant: ARIZONA BOARD OF REGENTS on behalf of ARIZONA STATE UNIVERSITY, Scottsdale, AZ (US)

(72) Inventors: Stuart Lindsay, Phoenix, AZ (US); Peiming Zhang, Gilbert, AZ (US); Yanan Zhao, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 62 days.

This patent is subject to a terminal disclaimer.

(21) Appl. No.: 15/797,052

(22) Filed: Oct. 30, 2017

(65) Prior Publication Data

US 2018/0120286 A1 May 3, 2018

Related U.S. Application Data

(63) Continuation-in-part of application No. 15/375,901, filed on Dec. 12, 2016, now Pat. No. 10,379,102.

(Continued)

(51) Int. Cl.
*G01N 27/327* (2006.01)
*G01N 33/487* (2006.01)
*G01N 27/447* (2006.01)

(52) U.S. Cl.
CPC . *G01N 33/48721* (2013.01); *G01N 27/44791* (2013.01)

(58) Field of Classification Search
CPC ................................................ G01N 33/48721
See application file for complete search history.

(56) References Cited

U.S. PATENT DOCUMENTS 6,391,558 B1 * 5/2002 Henkens ............. C12Q 1/6825
435/6.11
6,824,974 B2 11/2004 Pisharody et al.
(Continued)

FOREIGN PATENT DOCUMENTS

WO WO 2015/130781 A1 9/2015
WO WO 2015/131073 A1 9/2015
WO WO 2015/161119 A1 10/2015

OTHER PUBLICATIONS

Amdursky, N. et al., "Electronic Transport via Proteins," Adv Mater. 26(42): pp. 7142-7161 (2014).
(Continued)

*Primary Examiner* — Alexander S Noguerola
(74) *Attorney, Agent, or Firm* — Byrne Poh LLP; Nina R. Horan

(57) ABSTRACT

A single molecule sensing or detecting device includes a first electrode and a second electrode separated from the first electrode by a gap. The first electrode and the second electrode have an opening formed therethrough. At least one of the first electrode and the second electrode is functionalized with a recognition molecule. The recognition molecule has an effective length L1 and is configured to selectively bind to a target molecule having an effective length L2. The size of the gap is configured to be greater than 2L1, but less than or equal to the sum of 2L1 and L2.

14 Claims, 23 Drawing Sheets

Related U.S. Application Data

(60) Provisional application No. 62/266,282, filed on Dec. 11, 2015.

(56) References Cited

U.S. PATENT DOCUMENTS

| | | | |
|---|---|---|---|
| 7,785,785 | B2 | 8/2010 | Pourmand et al. |
| 8,628,649 | B2 | 1/2014 | Lindsay et al. |
| 8,753,893 | B2* | 6/2014 | Liu ................ B01L 3/5025 422/50 |
| 8,961,757 | B2 | 2/2015 | Nuckolls et al. |
| 8,968,540 | B2 | 3/2015 | Reinhart et al. |
| 9,140,682 | B2 | 9/2015 | Lindsay et al. |
| 9,274,430 | B2 | 3/2016 | Gyarfas et al. |
| 9,395,352 | B2 | 7/2016 | Lindsay et al. |
| 9,593,372 | B2 | 3/2017 | Lindsay et al. |
| 9,766,248 | B2 | 9/2017 | Lindsay et al. |
| 9,810,681 | B2 | 11/2017 | Lindsay et al. |
| 2003/0064390 | A1 | 4/2003 | Schulein et al. |
| 2006/0154489 | A1 | 7/2006 | Tornow et al. |
| 2009/0017571 | A1 | 1/2009 | Nuckolls et al. |
| 2009/0295372 | A1 | 12/2009 | Krstic et al. |
| 2011/0166034 | A1 | 7/2011 | Kwong et al. |
| 2012/0258870 | A1 | 10/2012 | Schwartz et al. |
| 2013/0302901 | A1 | 11/2013 | Lindsay et al. |
| 2015/0010935 | A1 | 1/2015 | Lindsay et al. |
| 2015/0142327 | A1 | 5/2015 | Ashcroft et al. |
| 2015/0144506 | A1 | 5/2015 | Lindsay et al. |
| 2016/0018384 | A1 | 1/2016 | Lindsay et al. |
| 2016/0025702 | A1 | 1/2016 | Lindsay et al. |
| 2016/0108002 | A1 | 4/2016 | Zhang et al. |
| 2016/0177383 | A1 | 6/2016 | Ashcroft et al. |
| 2016/0194698 | A1 | 7/2016 | Lindsay |
| 2016/0258925 | A1 | 9/2016 | Gyarfas et al. |
| 2016/0280723 | A1 | 9/2016 | Zhang et al. |
| 2017/0003245 | A1 | 1/2017 | Lindsay et al. |
| 2017/0016852 | A1 | 1/2017 | Lindsay et al. |
| 2017/0038369 | A1 | 2/2017 | Lindsay et al. |
| 2017/0067902 | A1 | 3/2017 | Zhang et al. |
| 2017/0137389 | A1 | 5/2017 | Zhang et al. |
| 2017/0204066 | A1 | 7/2017 | Lindsay et al. |
| 2017/0343558 | A1 | 11/2017 | Lindsay et al. |
| 2019/0004003 | A1 | 1/2019 | Merriman et al. |

OTHER PUBLICATIONS

Arielly, R. et al., "Real-Time Detection of Redox Events in Molecular Junctions," J Am Chem Soc. 136(6): pp. 2674-2680 (2014).
Artés, J. M. et al. "Transistor-like Behavior of Single Metalloprotein Junctions" Nano Lett., 2012, 12(6), pp. 2679-2684 (publication date (Web): Oct. 5, 2011).
Artes, J. M. et al., "Conductance Switching in Single Wired Redox Proteins," Small 10(13): pp. 2537-2541 (2014).
Bogomolny, E. et al., "Structure of Wave Functions of Pseudointegrable Billiards," Phys Rev Lett. 92: pp. 244102-1-244102-4 (2004).
Bogomolny, E. et al., "Models of intermediate spectral statistics," Phys Rev E. 59: pp. R1315-R1318 (1999).
Beratan, D. N. et al., "Charge Transfer in Dynamical Biosytems, or The Treachery of (Static) Images," Acc. Chem Res. 48(2): pp. 474-481 (2015).
Bertazzon, A. et al., "Scanning tunneling microscopy imaging of Torpedo acetylcholine receptor," Proc Natl Acad Sci. USA 89(20): pp. 9632-9639 (1992).
Chang, S. et al., "Gap Distance and Interactions in a Molecular Tunnel Junction," J Am Chem Soc. 133(36): pp. 14267-14269 (2011).
Chang, S. et al., "Palladium electrodes for molecular tunnel junctions," Nanotechnology 23(42): pp. 1-5 (2012).
Choi, Y. et al. "Site-specific inhibition of integrin alpha v beta 3-vitronectin association by a ser-asp-val sequence through an Arg-Gly-Asp-binding site of the integrin." Proteomics, vol. 10, Issue 1, No. 1 Jan. 2010, pp. 72-80 (First published Oct. 30, 2009).
Cui, X. D. et al. "Reproducible Measurement of Single-Molecule Conductivity" Science, vol. 294, Issue 5542, pp. 571-574 (Oct. 19, 2001).
Dong, X. et al., "Alpha(v)beta(3) Integrin Crystal Structures and Their Functional Implications," Biochemistry 51(44): pp. 8814-8828 (2012).
Engel, G. S. et al., "Evidence for wavelike energy transfer through quantum coherence in photosynthetic systems," Nature 446(7137): pp. 782-786 (2007).
Fan, F. R. F. et al., "Electrochemical Detection of Single Molecules," Science 267: pp. 871-874 (1995).
Grdeń, M. et al., "Electrochemical behavior of palladium electrode: Oxidation, electrodissolution and ionic adsorption," Electrochimca Acta. 53: pp. 7583-7806 (2008).
Haiss, W. et al., "Thermal gating of the single molecule conductance of alkanedithiols," Faraday Discussions 131: pp. 253-264 (2006).
Hoffman, R., "An Extended Hückel Theory I. hydrocarbons," J Chem Phys. 39: pp. 1397-1412 (1963).
Im, J. et al., "Electronic single-molecule identification of carbohydrate isomers by recognition tunneling," Nat Commun. 7: pp. 1-7 (2016).
Kumar, K. S. et al., "Long-Range Tunneling Processes across Ferritin-Based Junctions," Adv Mater. 28(9): pp. 1824-1830 (2016).
Leatherbarrow, R. J. et al., "Structure of Immunoglobulin G by Scanning Tunneling Microscopy," J Mol Biol. 221(2): pp. 361-365 (1991).
Lindsay, S. et al., "Recognition tunneling," Nanotechnology 21(26): pp. 1-12 (2010).
Lloyd, S., "Quantum coherence in biological systems," Journal of Physics: Conference Series 302: pp. 1-5 (2011).
Luo, B. H. et al., "Structural Basis of Integrin Regulation and Signaling," Annu Rev Immunol. 25: pp. 619-647 (2007).
Malvankar, N. S. et al., "Tunable metallic-like conductivity in microbial nanowire networks," Nat. Nanotechnol. 6(9): pp. 573-579 (2011).
O'Boyle, N. M. et al., "Open Babel: An pen chemical toolbox," J Cheminform. 3: pp. 1-14 (2011).
Onuchic, J. N. et al., "Pathway Analysis of Protein Electron-Transfer Reactions," Annu. Rev. Biophys Biomol Struct. 21, pp. 349-377 (1992).
Palecek, E. et al., "Electrochemistry of Nonconjugated Proteins and Glycoproteins. Toward Sensors for Biomedicine and Glycomics," Chem Rev. 115(5): pp. 2045-2108 (2015).
Pang, P. et al. "Fixed-Gap Tunnel Junction for Reading DNA Nucleotides" ACS Nano, 2014, 8 (12), pp. 11994-12003 (Publication Date (Web): Nov. 7, 2014).
Polizzi, N. F. et al., "Physical constraints on charge transport through bacterial nanowires," Faraday Discussions 153, pp. 43-62 (2012).
Sancey, L. et al., "Clustering and Internalization of Integrin alphavbeta3 With a Tetrameric RGD-synthetic Peptide," Mol Ther. 17(5): pp. 837-843 (2009).
Simmons, J. G., "Generalized Formula for the Electric Tunnel Effect between Similar Electrodes Separated by a Thin Insulating Film," J Appl Phys. 34(6): pp. 1793-1803 (1963).
Stuchebrukhov, A. A., "Towards AB Initio Theory of Long-Distance Electron Tunneling in Proteins: Tunneling Currents Approach," Adv Chem Phys. 118: pp. 1-44 (2001).
Thomson, N. H. et al., "Molecular images of cereal proteins by STM," Ultramicroscopy 42-44 (Part B): pp. 1204-1213 (1992).
Vattay, G. et al., "Quantum criticality at the origin of life," Journal of Physics: Conference Series 626: pp. 1-10 (2015).
Xiao, X. "Conductance Titration of Single-Peptide Molecules" J. Am. Chem. Soc. 2004, 126(17), pp. 5370-5371 (Publication Date (Web): Apr. 9, 2004).
Xiong, J. P. et al., "Crystal structure of the extracellular segment of integrin alpha Vbeta3 in complex with an Arg-Gly-Asp ligand," Science 296(5565): pp. 151-155 (2002).
Zhang, Y. et al., "Biological charge transfer via flickering resonance," Proc Natl Acad Sci. USA 111(28): pp. 10049-10054 (2014).
Zwolak, M. et al. "Electronic Signature of DNA Nucleotides via Transverse Transport" Nano Lett., 2005, 5(3), pp. 421-424 (Publication Date (Web): Feb. 12, 2005).

(56) References Cited

OTHER PUBLICATIONS

Notice of Allowance dated Mar. 29, 2019 in U.S. Appl. No. 15/375,901.
Office Action dated Dec. 10, 2018 in U.S. Appl. No. 15/375,901.
Pang et al., "Fixed-Gap Tunnel Junction for Reading DNA Nucleotides," ACSNano, 8(12), 2014, 11994-12003.
Roxin et al., "Flexible or fixed: a comparative review of linear and cyclic cancer-targeting peptides," Future Med. Chem, 4(12), 2012, 1601-1618.

* cited by examiner

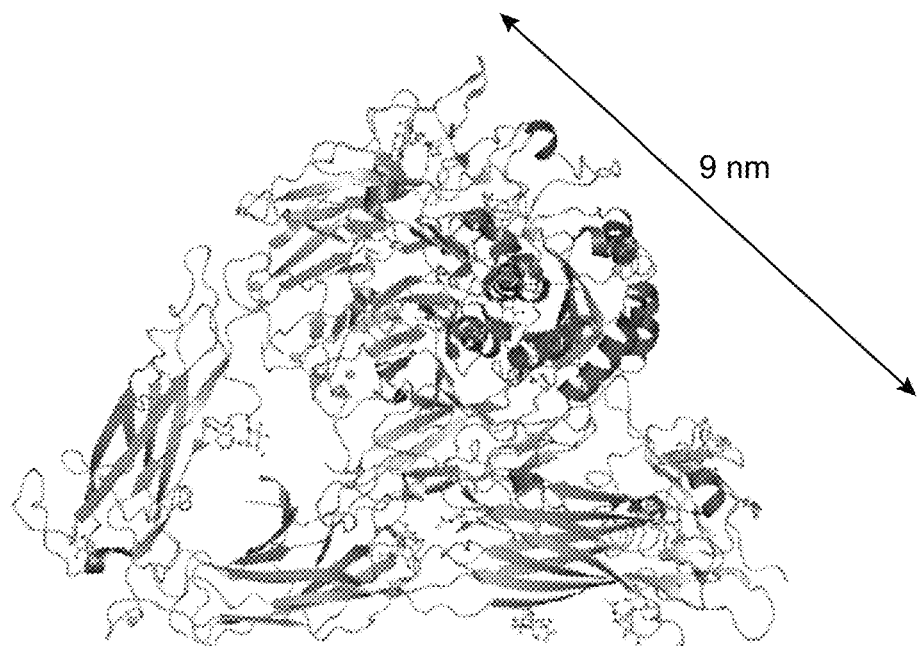
FIG. 3
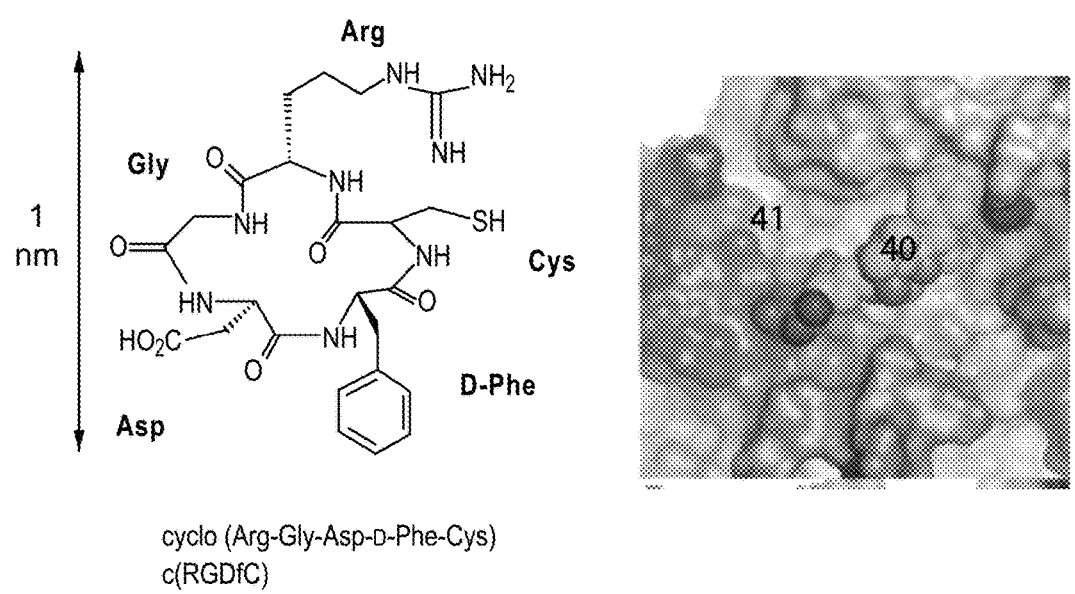
cyclo (Arg-Gly-Asp-D-Phe-Cys)
c(RGDfC)
FIG. 4A                    FIG. 4B

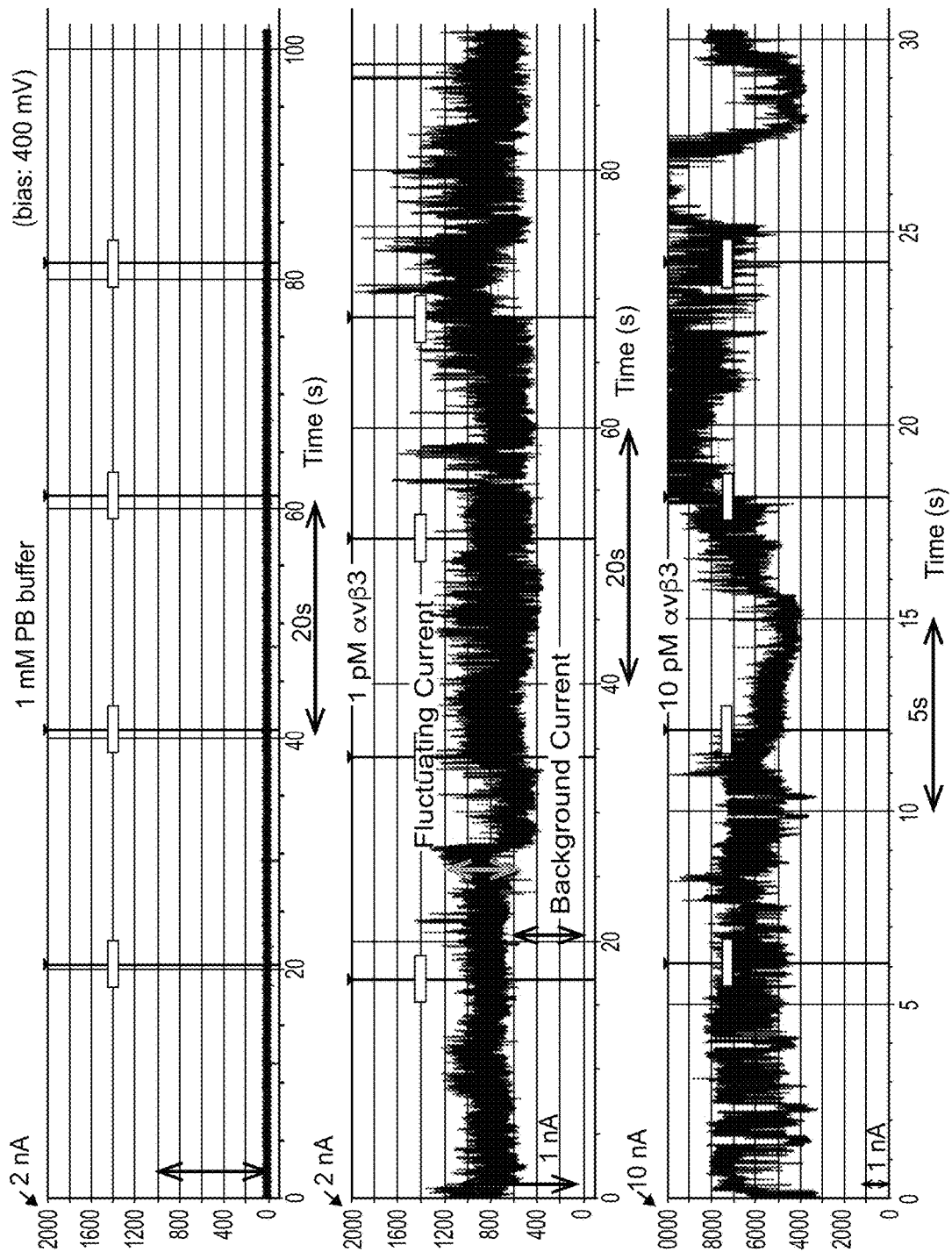

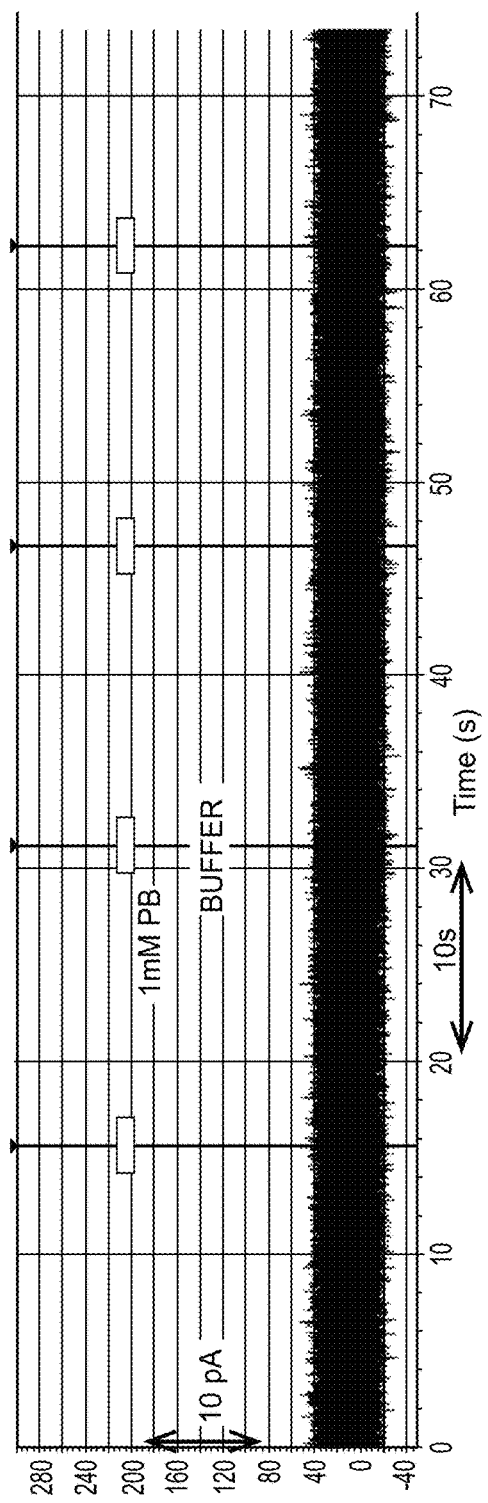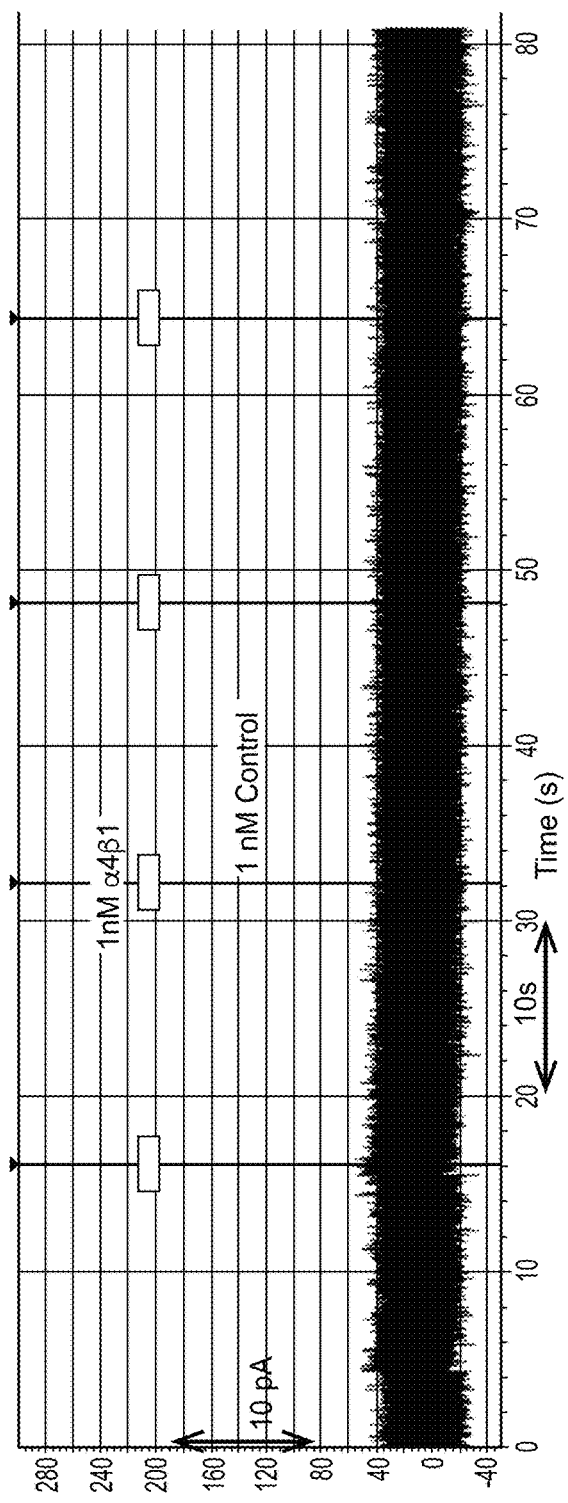

SYSTEM AND METHOD FOR SINGLE MOLECULE DETECTION

CROSS-REFERENCE TO RELATED APPLICATIONS

This application is a continuation-in-part application of U.S. application Ser. No. 15/375,901, filed on Dec. 12, 2016, which claims priority to and the benefits of U.S. Provisional Application No. 62/266,282, filed on Dec. 11, 2015, the contents of each of which are incorporated herein by reference in their entireties.

GOVERNMENT RIGHTS

This invention was made with government support under R01 HG006323 awarded by The National Institutes of Health. The government has certain rights in the invention.

ABSTRACT OF THE DISCLOSURE

The present disclosure presents systems, methods and devices for detecting single molecules by direct electronic measurement as they bind a cognate ligand. In some embodiments, high contrast signals are produced with no labels and sample concentrations in the femtomolar range.

BACKGROUND

Electron tunneling is, in principle, sensitive to the presence of a molecule in a tunnel gap formed between two closely spaced metal electrodes (Zwolak and Di Ventra 2005). However, in practice, tunnel gaps are quite insensitive to molecules that may be trapped between the electrodes because the inevitable hydrocarbon contamination of metal electrodes outside of an ultrahigh vacuum clean environment makes for a poor contact between the electrodes and the molecules.

It has been shown that reproducible and characteristic electrical signals can be obtained if molecules are chemically attached to each electrode forming a tunnel junction, by, for example, sulfur-metal bonds (Cui, Primak et al. 2001). Such permanent connections, however, do not make for versatile detectors because the molecule that bridges the gap must be modified at two sites with groups such as thiols. Pishrody et al. (Pishrody, Kunwar et al. 2004), proposed a solution in which electrode pairs were functionalized with molecules that did not, by themselves bridge the gap, but rather, formed a bridged structure when a target molecule became bound. This prior art is illustrated in FIG. 1. As shown, a first metal electrode 10 and a second metal electrode 12 are separated by a dielectric layer 16 with the electrode gap exposed at the edge of the layered device. A first recognition molecule 14a and a second recognition molecule 14b are chemically tethered to the electrodes by reactive groups 18. The molecules 14a and 14b are chosen so as to bind a target molecule 20 in such a way as to form a bridge across the gap between the electrodes when 20 binds both 14a and 14b. For example 14a and 14b may be composed of DNA oligomers chosen so have a sequence that, taken together, is complementary to a target DNA molecule 20. However, the simple device of FIG. 1 cannot be used as a single molecule detector, but rather, only as a system of a large number of such devices functionalized with many pairs of recognition molecules. In this way, the presence of certain molecules in a sample could be determined upon the measurement of current from many binding events.

U.S. publication no. 2010/0084276 (Lindsay et al.) discloses a device designed for sequencing polymers, such as DNA. In some embodiments of this prior art, as illustrated in FIG. 2, two closely spaced electrodes 30, 31 are separated by dielectric layer 33. A nanopore 34 is then drilled through the structure and the exposed electrodes functionalized with recognition molecules 35. The molecules bind to a target analyte 36 at two separate sites. Thus, once an analyte molecule enters the pore, it brings together the recognition molecules to form a connected pathway across the gap. The approach of such embodiments differ from that of Pishrody at least because (a) the nanopore of Lindsay et al. permits only one analyte to enter at a time (e.g., so that a polymer may be sequenced, as each chemical unit of the polymer enters the pore and generates a characteristic signal), and (b) the gap between the electrodes 30 and 31 is sized such that that single molecule binding event generates a large current.

SUMMARY OF SOME OF THE EMBODIMENTS OF THE DISCLOSURE

It is an object of at least some of the embodiments of the present disclosure to provide a device that detects single molecule binding events by, for example, direct electronic detection of binding on only a single ligand, e.g., such as an antibody.

In one aspect, the present disclosure provides a sensing device including a first electrode and a second electrode separated from the first electrode by a gap, where: the first electrode and the second electrode include an opening formed therethrough, at least one of the first electrode and the second electrode is functionalized with a recognition molecule, the recognition molecule has an effective length $L1$ and is configured to selectively bind to a target molecule having an effective length $L2$, and the size of the gap is configured to be greater than $2L1$, but less than or equal to the sum of $2L1$ and $L2$.

In another aspect, the present disclosure provides a method for detecting a target molecule in the sensing device provided herein, the method comprising recording a first current over time when a solution suspected of having the target molecule is in contact with the sensing device, obtaining a distribution of amplitudes of the first current, comparing the distribution of amplitudes with a reference distribution, and determining that the target molecule is detected if the distribution of amplitudes is substantially different from the reference distribution in shape. In some embodiments, the reference distribution is obtained by recording a second current over time when a test solution is in contact with the sensing device, and the test solution is substantially free of the target molecule.

In some embodiments, the method further comprises obtaining a mean baseline value for the second current recorded over time.

In some embodiments, the distribution of amplitudes is substantially different from the reference distribution when the distribution of amplitudes includes features of a constant current height above the mean baseline value.

In some embodiments, the distribution of amplitudes or the reference distribution is obtained by sampling amplitudes at a time interval of about 0.01 microseconds to 1 second.

In some embodiments, the constant current height is about 1 picoamp to 1 microamp.

In some embodiments, the distribution of amplitudes cannot be fitted by a single Gaussian.

In some embodiments, the reference distribution can be fitted by a single Gaussian.

In some embodiments, the distribution of amplitudes is substantially different from the reference distribution when the distribution of amplitudes cannot be fitted by a single Gaussian and the reference distribution can be fitted by a single Gaussian.

In yet another aspect, the present disclosure provides a method for detecting a target molecule in the sensing device provided herein, the method comprising: recording a first distribution of current signals when a test solution substantially free of the target molecule is in contact with the sensing device; contacting a sample solution suspected of having the target molecule with the sensing device; recording a second distribution of current signals when the sample solution is in contact with the sensing device; and determining that the target molecule is present in the sample solution when the second distribution has a different shape as compared to the first distribution.

In some embodiments, the first distribution can be fitted by a single Gaussian.

In some embodiments, the second distribution cannot be fitted by a single Gaussian.

In some embodiments, the target molecule is a protein, DNA, or RNA.

BRIEF DESCRIPTION OF THE FIGURES

FIG. 3 illustrates a model of $\alpha_V\beta_3$ integrin.

FIGS. 4A-B illustrate (FIG. 4A) Cyclic RGD peptide. (FIG. 4B) Binding site of RGD peptide at the junction of the $\alpha$ and $\beta$ subunits of integrin.

(FIG. 5B) Typical current trace when an integrin is captured as the probe is withdrawn.

(FIG. 6B) Distribution of withdrawal distances to the peak signal (the starting gap, 0 on this plot, is 2.7 nm).

FIGS. 9A-9C illustrate current data from a device according to some embodiments, in buffer solution (FIG. 9A) and then after adding 1 pM (FIG. 9B), and then 10 pM (FIG. 9C) of $\alpha_V\beta_3$ integrin.

FIGS. 10A-10B illustrate control signals (FIG. 10A, buffer, FIG. 10B, $\alpha_4\beta_1$ integrin) for a nanopore device according to some embodiments of the present disclosure into which only a single molecule can be received.

(FIG. 14A) schematic layout of the experiment. The probe tip and the substrate were functionalized with a cysteine-containing cyclic RGD peptide that binds $\alpha_V\beta_3$ integrin but not $\alpha_4\beta_1$. Electrodes were biased with respect to an Ag/AgCl reference connected via a salt bridge. Cyclic voltammetery on 0.5 cm$^2$ Pd-coated substrate modified with cyclic RGD peptide (inset) in 1 mM phosphate buffer (FIG. 14B) and after the addition of 10 nM $\alpha_V\beta_3$ (FIG. 14C). Logarithm of current vs retraction distance ($\Delta Z$) for solutions containing 10 nM $\alpha_V\beta_3$ (FIG. 14D) or $\alpha_4\beta_1$ (FIG. 14E). Inset in FIG. 14E shows the rapid decay of current in buffer alone as the tip is retracted from its initial set-point (4 pA at 200 mV, corresponding to about 2 nm).

(FIG. 15C) The distribution of charge in each peak (obtained by integrating each current-time curve) for the two proteins. The scale is logarithmic in charge.

(FIG. 16A) shows the layered structure of the MEMED with an opening that exposes the electrodes to the solution, sized (in this illustration) so as to trap just one integrin molecule. Electrodes are functionalized with cyclic RGD peptide and biased as shown. (FIG. 16B) TEM image of a cross section of the junction showing the 4.8 nm dielectric layer. (FIG. 16C) TEM image of a "T" shaped top electrode that was milled with three RIE-etched slots (white openings). (FIG. 16D) Typical current trace in phosphate buffer. The high baseline current comes from stray leakage paths, and the noise distribution (FIG. 16E) is well-described by a single Gaussian. When the control protein, $\alpha_4\beta_1$ was added (FIG. 16F) the noise distribution did not change. When $\alpha_V\beta_3$ protein was added (FIG. 16H) large current jumps to well defined levels (FIG. 16I) were observed. The background leakage was also reduced (as was observed in the cyclic voltammetry) indicating that the adsorbed protein passivates the surface.

(FIG. 17A) Some selected current traces, showing the onset of current jumps above the baseline leakage, starting at a bias of 100 mV, with fluctuations increasing as bias is increased (amplitude histograms are plotted to the right of each trace to the same current scale as each trace). Note that the current scales are different for each trace to show detail. The background leakage increases linearly with bias. (FIG. 17B) Scatter plot of the separation of peaks in the amplitude histograms as a function of bias. Sets of identical symbols at a given bias show the analysis for a particular run of signal, so that the spread of points represents the variations from burst to burst of signal in a given recording. Data are from 2 chips, chip 6(a-e) and chip 7(f,g). Points d are for a first run with chip 6, and a,b, and c are a for a second run. Here the b points are for a second peak in the distribution, and c are for a third peak. Runs were taken at a bias with respect to the reference of 0V except for e, and f which were taken at +50 mV. (FIG. 17C) Distribution (gray bars) of charge under each signal peak for the chip data at 300 mV (gray) and for the STM data at 200 mV (red data). Over these ranges of potential and bias, both electrodes were in a region that avoids Faradaic currents.

(FIG. 18A) The short-time distribution of "on" times is Poisson and identical for two values of bias. (FIG. 18B) The fraction of time spent in the "on" state as a function of bias (red squares). Additional black points are for the sharp additional features that appear as the larger current steps in the histograms at 250 and 300 mV, possibly representing binding of more than one molecule in the junction. (FIGS. 18C, 18D) Showing scatter plots of "on" time vs. amplitude of the current peak for individual signal events. The time scales are logarithmic so the linear fits (red lines) demonstrate an exponential relationship between peak current and on-time. The fitted slope is 0.006 $pA^{-1}$ in each case.

DETAILED DESCRIPTION OF EMBODIMENTS OF THE PRESENT DISCLOSURE

Figure 1:
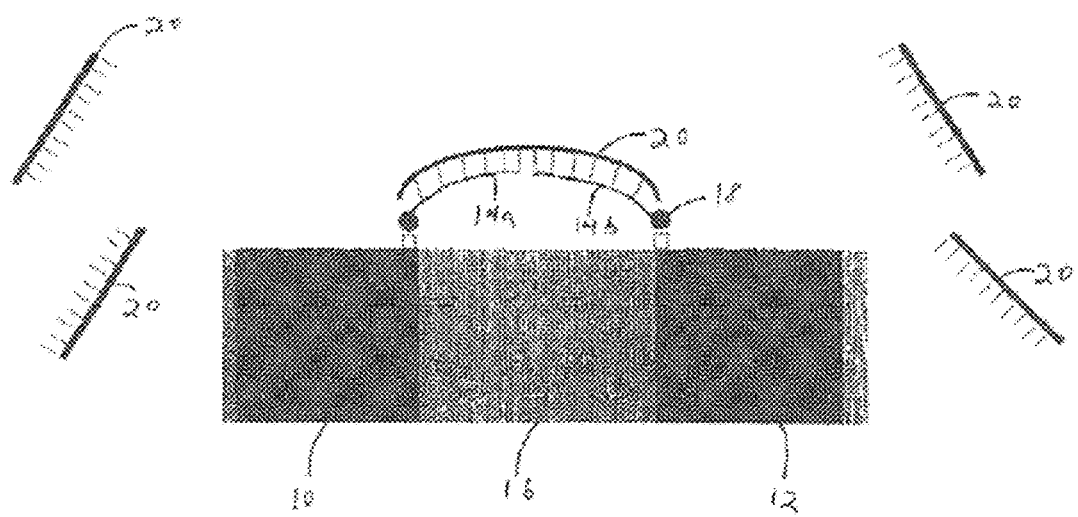
FIG. 1 illustrates a bridged electrode pair according to the prior art.
Figure 2:
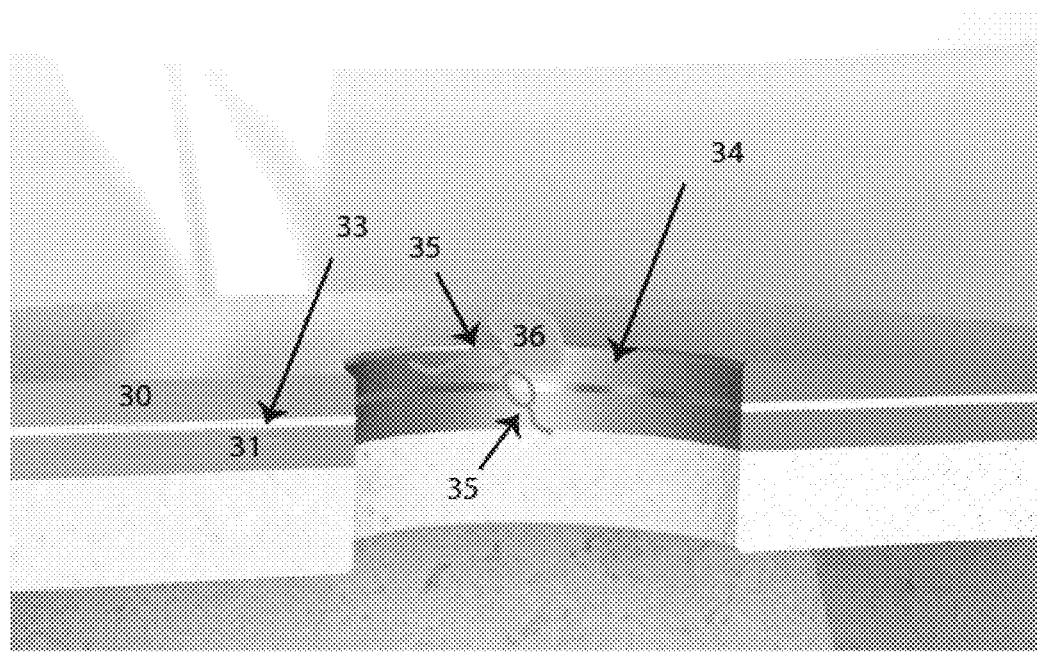
FIG. 2 illustrates a bridged electrode pair within a nanopore according to the prior art.

In one aspect, the present disclosure provides a sensing device including a first electrode and a second electrode separated from the first electrode by a gap, where: the first electrode and the second electrode include an opening formed therethrough, at least one of the first electrode and the second electrode is functionalized with a recognition molecule, the recognition molecule has an effective length L1 and is configured to selectively bind to a target molecule having an effective length L2, and the size of the gap is configured to be greater than 2L1, but less than or equal to the sum of 2L1 and L2.

A single molecule sensing or detecting device includes a first electrode and a second electrode separated from the first electrode by a gap. The first electrode and the second electrode have an opening formed therethrough. At least one of the first electrode and the second electrode is functionalized with a recognition molecule. The recognition molecule has an effective length L1 and is configured to selectively bind to a target molecule having an effective length L2. In some embodiments, the size of the gap is configured to be greater than L2, but less than or equal to the sum of L1 and L2. In some embodiments, the size of the gap is configured to be greater than 2L1, but less than or equal to the sum of 2L1 and L2.

In some embodiments, the device further includes an insulating layer disposed in the gap, wherein a thickness of the insulating layer is less than or equal to the sum of L1 and L2. In some embodiments, the size of the gap is at least twice the effective length L1. In some embodiments, the size of the gap is equal to the sum of L1 and L2. In some embodiments, the size of the gap is between about 2 nm to about 15 nm. In some embodiments, the size of the gap is between about 2 nm to about 10 nm. In some embodiments, the size of the gap is between about 5 nm to about 15 nm. In some embodiments, the recognition molecule includes any suitable peptide such as, for example, a cyclic RGD peptide. In some embodiments, the size of the opening is between 0.1 nm and 100 microns in a linear dimension.

In some embodiments, the first electrode and/or the second electrode are configured to generate a current upon binding of the target molecule. The current includes a fluctuating portion and/or a background portion. In some embodiments, the background portion of the current is based on a number of non-target molecules adsorbed on the first electrode and/or on the second electrode. In some embodiments, the fluctuating portion is based on a concentration of the target molecule in a solution containing the target molecule, the solution in contact with the first electrode and the second electrode, and the concentration of the target molecule in the solution is from about 10 fM to about 1 µM.

In some embodiments, a method for sensing or detecting a target molecule includes applying a voltage bias across a first electrode and a second electrode of a molecular sensing or detecting device. The first electrode and second electrode collectively have an opening formed therethrough. The second electrode separated from the first electrode by a gap, and at least one of the first electrode and the second electrode is functionalized with a recognition molecule. The recognition molecule includes an effective length L1 and is configured to selectively bind to a target molecule having an effective length L2. The method also includes contacting the first electrode and the second electrode with a solution containing the target molecule in a concentration from about 10 fM to about 1 µM. The method also includes monitoring current generated between the first electrode and the second electrode over time. The method also includes determining one or more of: the presence of the target molecule; and a number of non-target molecules adsorbed on the first electrode and/or on the second electrode.

In some embodiments, determining the presence of the target molecule is based on a fluctuating portion of the current. In some embodiments, determining a number of non-target molecules adsorbed on the first electrode and/or on the second electrode is based on a background portion of the current. In some embodiments, the device further includes an insulating layer disposed in the gap, and a thickness of the insulating layer is less than or equal to the sum of L1 and L2. In some embodiments, the thickness of the insulating layer is less than or equal to the sum of 2L1 and L2. In some embodiments, the gap is at least twice the effective length L1 in thickness. In some embodiments, the size of the gap is equal to the sum of L1 and L2. In some embodiments, the size of the gap is between about 2 nm to about 15 nm. In some embodiments, the size of the gap is between about 2 nm to about 10 nm. In some embodiments, the size of the gap is between about 5 nm to about 15 nm. In some embodiments, the recognition molecule includes a peptide. In some embodiments, the peptide is a cyclic RGD peptide. In some embodiments, the target molecule is a protein, DNA, or RNA.

In another aspect, the present disclosure provides a method for detecting a target molecule in the sensing device provided herein, the method comprising recording a first current over time when a solution suspected of having the target molecule is in contact with the sensing device, obtaining a distribution of amplitudes of the first current, comparing the distribution of amplitudes with a reference distribution, and determining that the target molecule is detected if the distribution of amplitudes is substantially different from the reference distribution in shape. In some embodiments, the reference distribution is obtained by recording a second current over time when a test solution is in contact with the sensing device, and the test solution is substantially free of the target molecule. In some embodiments, the test solution is substantially free of the target molecule when it does not include the target molecule.

In some embodiments, the method further comprises obtaining a mean baseline value for the second current recorded over time.

In some embodiments, the distribution of amplitudes is substantially different from the reference distribution when the distribution of amplitudes includes features of a constant current height above the mean baseline value.

In some embodiments, the distribution of amplitudes cannot be fitted by a single Gaussian. In some embodiments, the reference distribution can be fitted by a single Gaussian. In some embodiments, the distribution of amplitudes is substantially different from the reference distribution when the distribution of amplitudes cannot be fitted by a single Gaussian and the reference distribution can be fitted by a single Gaussian. Methods of fitting a distribution by a Gaussian are well known in the art.

In some embodiments, the distribution of amplitudes or the reference distribution is obtained by sampling amplitudes at a time interval of about 0.01 microseconds to 1 second. For example, the time interval can be about 0.01 microseconds to 1 microsecond, about 0.01 microseconds to 10 microsecond, or about 0.01 microseconds to 100 microseconds.

In some embodiments, the constant current height is about 1 picoamp to 1 microamp. For example, the constant current height can be about 10 picoamp to 100 picoamp, about 10 picoamp to 1000 picoamp, about 100 picoamp to 1 nanoamp, about 1 nanoamp to 10 nanoamps, about 1 nanoamp to 100 nanoamp, or about 1 nanoamp to 1 microamp.

In a similar aspect, the present disclosure provides a method for detecting a target molecule in the sensing device provided herein, the method comprising: recording a first distribution of current signals when a test solution substantially free of the target molecule is in contact with the sensing device; contacting a sample solution suspected of having the target molecule with the sensing device; recording a second distribution of current signals when the sample solution is in contact with the sensing device; and determining that the target molecule is present in the sample solution when the second distribution has a different shape as compared to the first distribution.

In some embodiments, the second distribution has a different shape as compared to the first distribution when the first distribution can be fitted by a single Gaussian and the second distribution cannot be fitted by a single Gaussian.

It is commonly assumed that proteins are excellent insulators. Direct measurements of the conductance of small peptides (i.e., short protein fragments) in their linear form shows that current decays very rapidly with an increase in the length (i.e., number of amino acid residues) of the peptide (Xiao, Xu et al. 2004). However, scanning-tunneling microscope studies of electron-transfer proteins (Ulstrup 1979, Artes, Diez-Perez et al. 2012), can show remarkably large conductance values. While these values are impossible to reconcile with the short electronic decay lengths measured in peptides, it has recently been suggested that many proteins, in their three dimensional, folded form, are poised in a critical state between being a bulk conductor (metal-like) and an insulator, such that local fluctuations can drive proteins into states that are transiently conductive (Vattay, Salahub et al. 2015). Accordingly, some embodiments of the present disclosure are disclosed which enable proteins to form highly conductive bridges across gaps between electrodes that are much larger than could possibly support electron tunneling currents. Even with the most favorable electronic properties of a molecule in a tunnel junction, tunnel conductances drop below femtoseimens for distances of 3 to 4 nm. Such large gaps provide, in at least some embodiments, a large current signal, even when the target protein is bound to only one electrode by a recognition reagent, with currents corresponding to nanoseimens of conductance.

EXAMPLES

Example 1

To illustrate the process, the example of $\alpha_V\beta_3$ integrin, which comprises two subunits (the $\alpha$ and $\beta$ chains) that meet at the apex of pyramidal shape that is about (in some embodiments) 9 nm high (FIG. 3) is used. This protein is strongly bound by a cyclic RGB peptide (FIG. 4A) at a unique site near the apex of the pyramidal shape (FIG. 4B). In FIG. 4B, 41 is the junction between the $\alpha$ and $\beta$ chains and 40 is the cyclic RGD peptide (Choi, Kim et al. 2010). The peptide is relatively small being about 1 nm across its widest folded dimension.

Figure 5A:
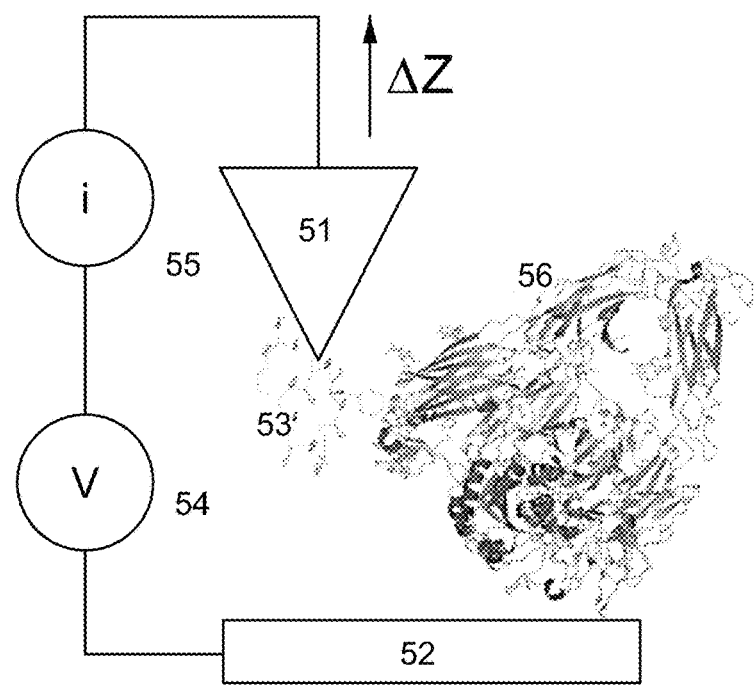
FIGS. 5A-5B illustrates (FIG. 5A) Scanning tunneling microscope experiment to demonstrate capture of $\alpha_V\beta_3$ integrin with functionalization of just one electrode.
Figure 5B:
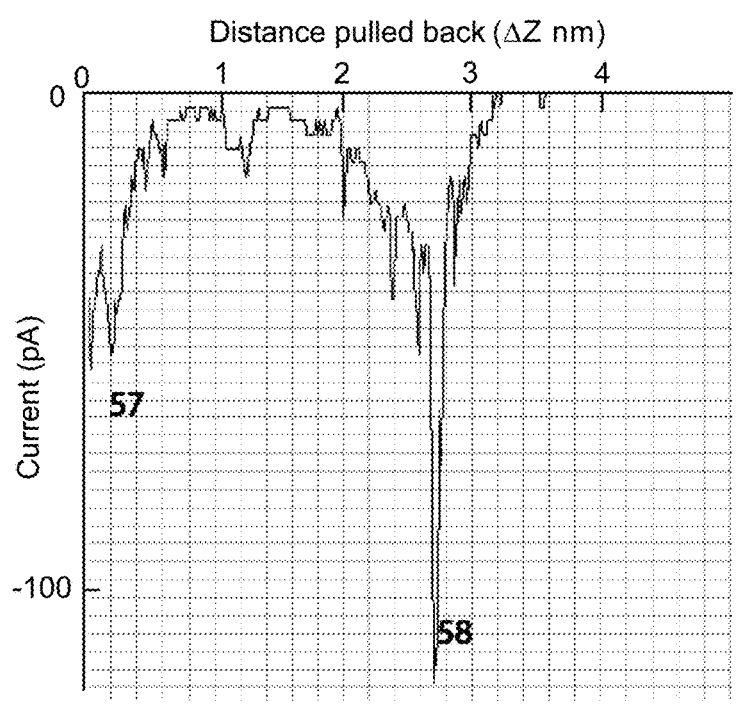

Accordingly, in some embodiments, functionalizing just one of a pair of electrodes generates a unique electrical recognition signal for a corresponding molecule(s). To do this, a scanning tunneling microscope (STM) was used (see STM, FIG. 5A), where a gold probe 51 was functionalized with the RGD peptide 53 via the chemical interaction between the cysteine residue and the gold. The probe was positioned at a set point bias (V) and current (I) such that the apex of the probe was held approximately 2.7 nm above a bare gold substrate, 52. As the probe was pulled away an extra distance ΔZ from the surface, a decaying current could be observed during some of the experiments (e.g., feature 57 in FIG. 5B). However, in the absence of the $\alpha_V\beta_3$ integrin, no other features were observed, even if fairly high concentrations (e.g., 100 nM) of a protein such as BSA were added to the solution in the STM. Once 100 nM $\alpha_V\beta_3$ integrin 56 was added to the solution, a new feature appeared as a current peak away from the origin 58 in FIG. 5B.

Figure 6A:
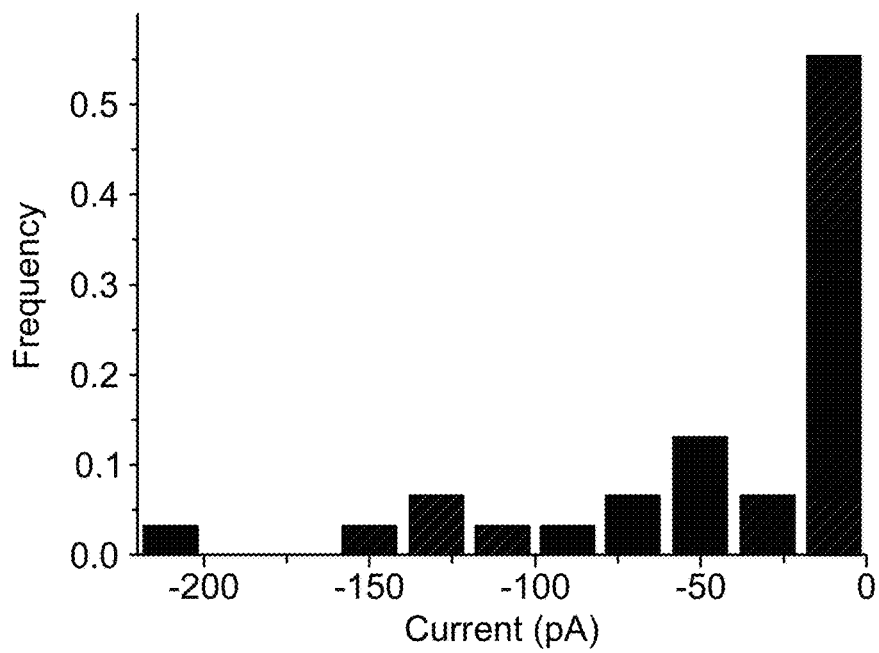
FIGS. 6A-6B illustrate (FIG. 6A) histogram of current peak values for integrin capture (current is shown increasing negative to the left here).
Figure 6B:
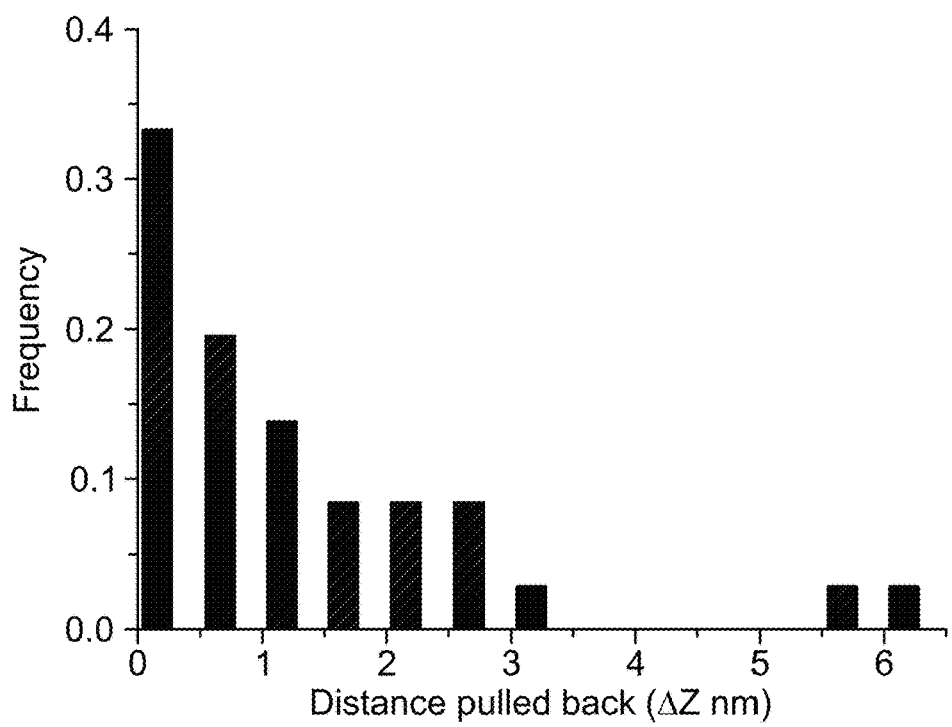

A statistical analysis of the distribution of features in terms of the peak current (FIG. 6A) and distance above approximately 2.7 nm for which a peak occurs (ΔZ in FIG. 6B) shows that signals of many tens of picoamps are generated at distances of about 3 nm to about 6 nm overall (2.7 nm +ΔZ). In contrast to conventional tunneling signals, these signals peak when the probe is some distance away from the surface, signifying that the probe has captured a conductive particle. Importantly, no such features were seen in the absence of the $\alpha_v\beta_3$ integrin, or in the presence of a protein (BSA) that does not bind the cyclic RGD peptide.

Figure 7:
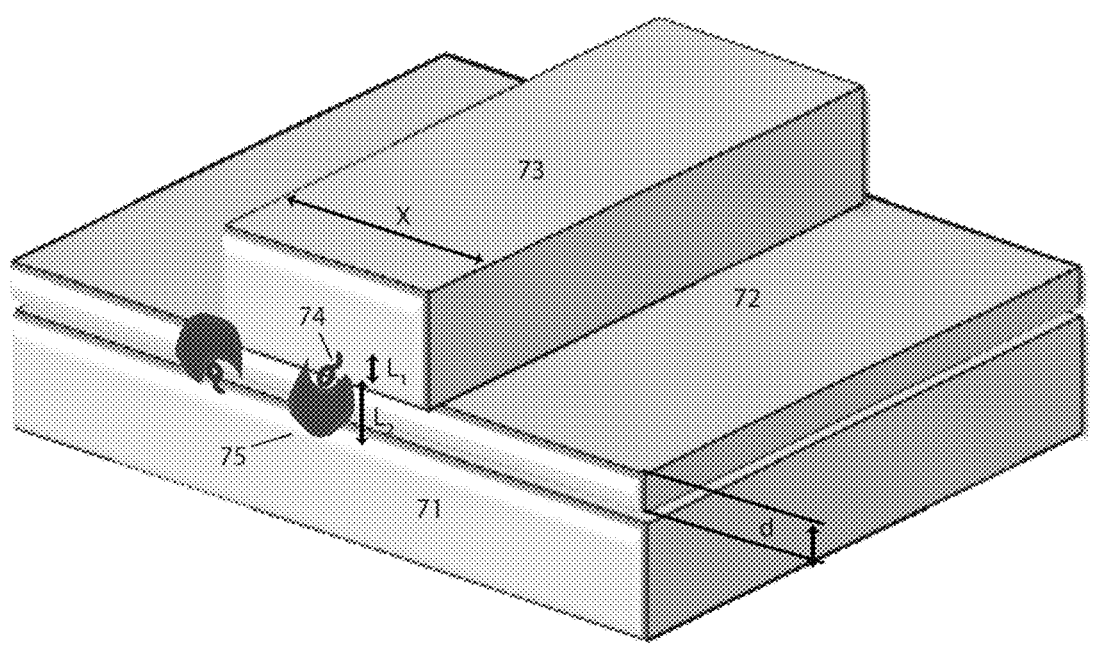
FIG. 7 illustrates a cross-sectional view of a tunnel junction edge of a device as exposed by an opening, according to some embodiments of the present disclosure.

FIG. 7 illustrates a cross-sectional view of a tunnel junction edge (i.e., the edge of an opening) of the device according to some embodiments of the present disclosure which includes a first metal electrode 71 (e.g., palladium, gold and/or platinum) onto which is deposited a layer of an insulating dielectric such as alumina 72 (for example). A second metal electrode 73 is then deposited, typically using one of the metals used for the first electrode. In some embodiments (not shown), the first electrode 71 and the second electrode 73 A cut is then made in the structure to expose the edge of these layers (fabrication of this type of device is described in detail in co-pending, published WO2015/161119, and also in Pang, Ashcroft et al. 2014) to form the opening/nanopore 78, shown here as a plane adjacent to the electrodes 71, 73. Accordingly, the first electrode 71 and the second electrode 73 can have an opening formed therethrough such as, for example, a nanopore. Said another way, the first electrode 71 and the second electrode 73 can be said to be arranged within or adjacent to an opening, or have a nanopore formed therethrough.

Figure 8:
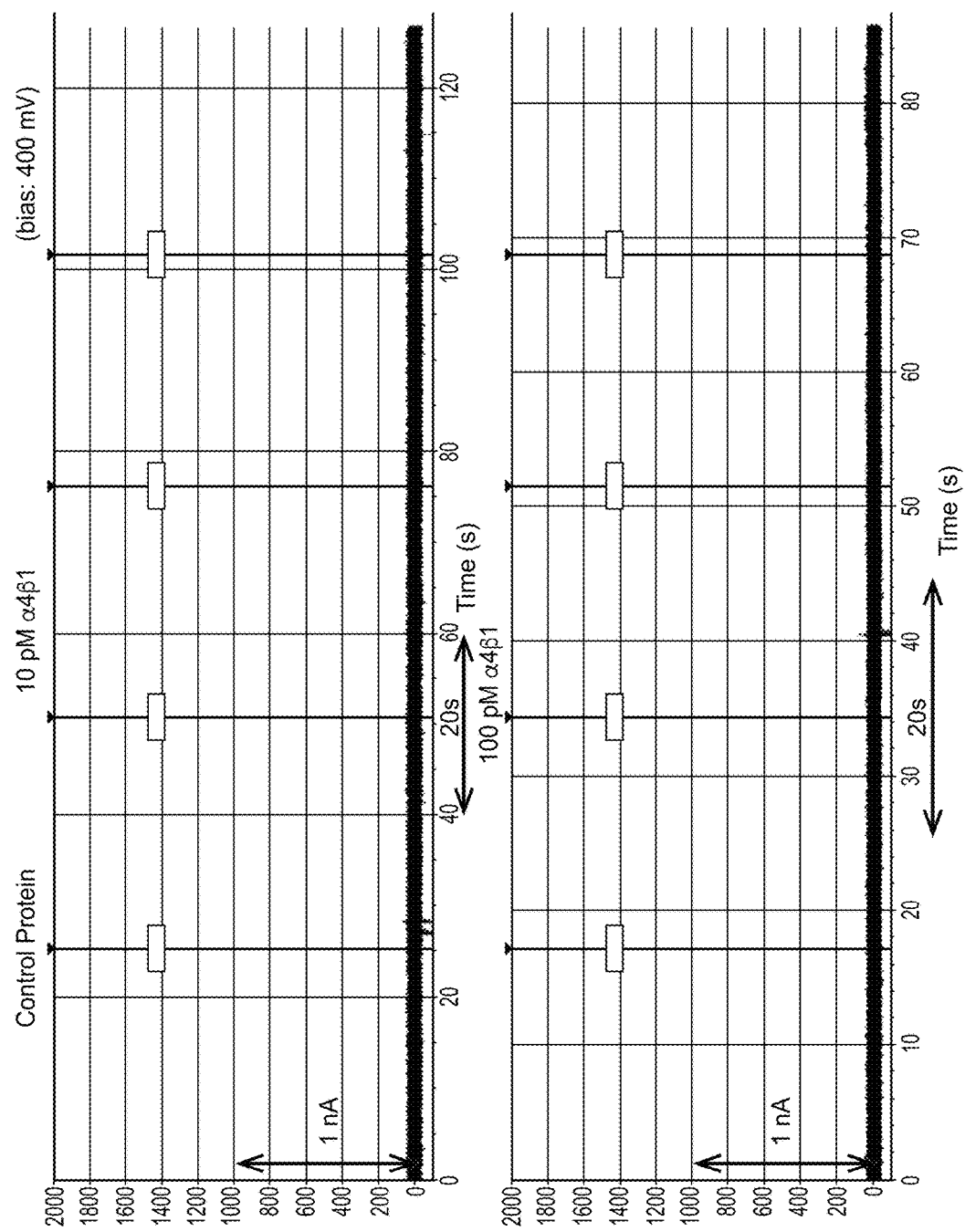
FIG. 8 illustrates current data recorded for two concentrations of $\alpha_4\beta_1$ integrin, a molecule not bound by the RGD peptide with a device according to some embodiments.

In some such embodiments (of those illustrated in, e.g., FIG. 7), it is a particular feature of such embodiments in the use of, depending upon the embodiments, either or both of (a) recognition molecules that bind a target at only one site, so that the geometric constraints of forming a chemical bridge do not apply, and (b) a choice of dimensions that gives a very high signal-to-background ratio. Specifically, for example, the insulating layer 72 is deposited with a thickness d that is chosen to be greater than the longest linear dimension of the recognition molecules 74 ($L_1$, referred to as its effective length). However, according to some embodiments, it is chosen to be less than the combined overall length of the largest dimension of a target molecule 75 ($L_2$, also referred to as its effective length) bound to the recognition molecule 74 ($L_1+L_2$). In the case of the integrin-RGD pair (FIGS. 3 and 4) the RGD molecule is about 1 nm at its longest, while the integrin is 9 nm, for a total of about 10 nm. This is a distance over which electron tunneling currents generally do not flow because the tunneling probability would be infinitesimal. However, a large particle that fluctuates into a highly conductive state could be used to mediate current flow (Vattay, Salahub et al. 2015). In some embodiments, the gap need only be made substantially larger than twice the largest dimension of the recognition molecules (i.e., $>2L_1$). Thus, for example, if a recognition molecule is 1 nm at its longest dimension, then the gap is configured to be greater than 2 nm, preferably by about 10%, to accommodate variations in the junction geometry (larger than 2.2 nm in this example). In some embodiments, a gap size can be from the noted minimum up to the size of one recognition molecule plus the size of the target protein. For example, if the largest dimension of the protein is 9 nm, then the gap in this case can be as big 9 nm plus the size of one of the recognition molecules (1 nm in this example), thus, a gap of 10 nm. In experiments, devices functionalized with the cyclic RGD peptide and fabricated with a gap d of 3.5 to 4 nm show no background current, which continues to be the case even when the junctions are exposed to a homologous protein ($\alpha_4\beta_1$ integrin) that does not bind the RGD peptide. FIG. 8 shows current-vs time traces for devices in contact with 10 pM (a) and 100 pM (b) solutions of $\alpha_4\beta_1$ integrin.

However, when the junctions are exposed to the target protein ($\alpha_v\beta_3$ integrin) signals appear immediately. FIGS. 9A-9B shows (FIG. 9A) the signal in 1 mM phosphate buffer (pH 7.0) just before the addition of a 1 pM solution of $\alpha_v\beta_3$ integrin in the same buffer solution (FIG. 9B). A clear signal is immediately generated which includes two (2) features as marked: a background current (of about 0.5 nA in this case) and noise spikes of 0.5 to 1 nA superimposed on top. On increasing the concentration of $\alpha_v\beta_3$ integrin to 10 pM, the background current increases by nearly an order of magnitude (while the fluctuations remain generally constant).

Figure 11:
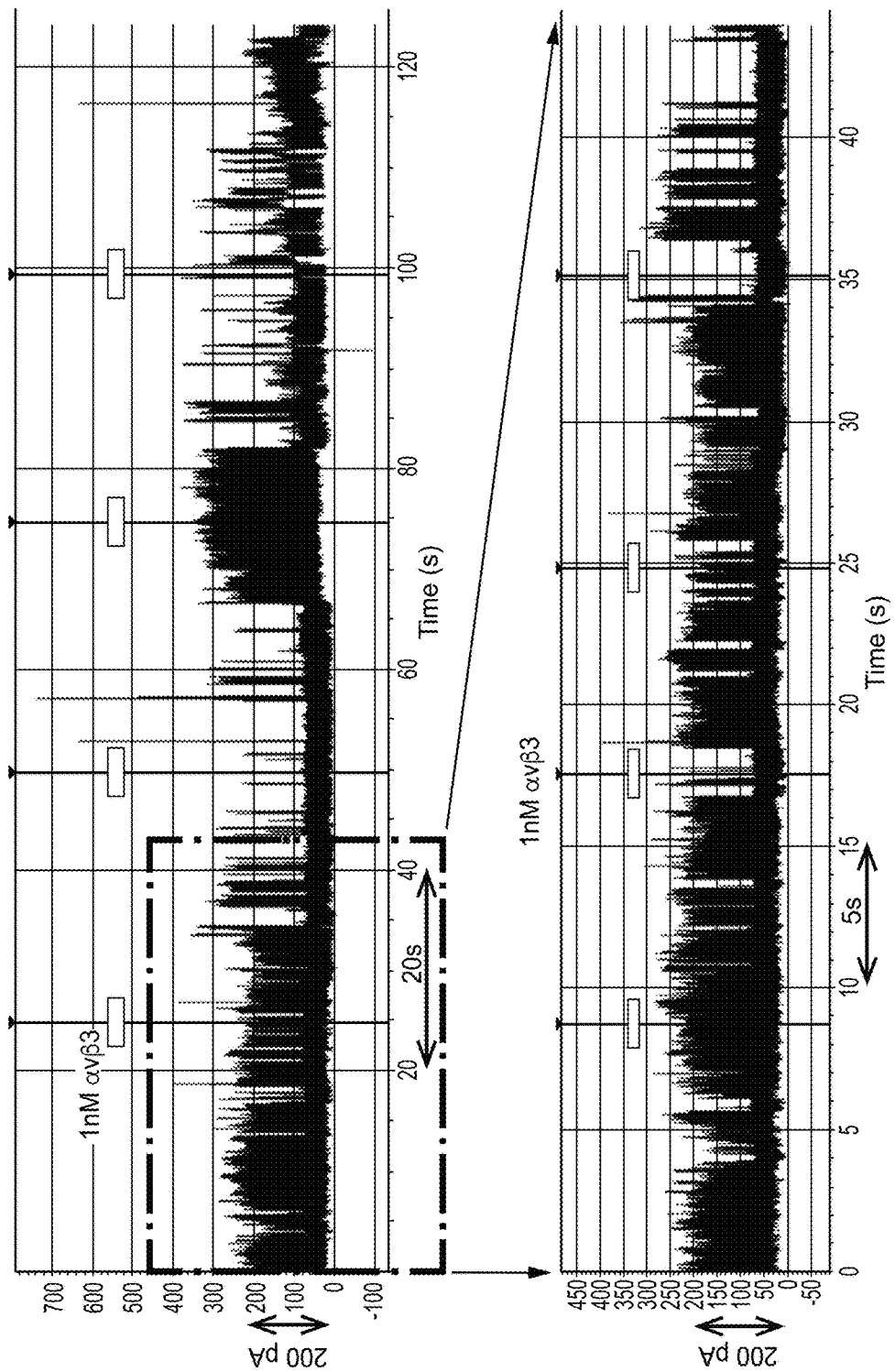
FIG. 11 illustrates a signal obtained when 1 nM $\alpha_V\beta_3$ integrin was placed in contact with the nanopore device according to some embodiments of the disclosure.

Accordingly, in some embodiments, the background signal corresponds to the number of molecules adsorbed on the electrodes. This can be substantiated by collecting signals from a device small enough to allow only one integrin molecule to be trapped. In such a device, experiments were performed where the electrode edges were exposed by drilling a nanopore of approximately 12 nm diameter through the junction device. The electrodes were functionalized again with the cyclic RGD peptide. FIGS. 10A-10B show that in phosphate buffer (FIG. 10A) or in the presence of a 1 nM solution of the non-binding control ($\alpha_4\beta_1$ integrin, FIG. 10B) no signals are generated. However, when 1 nM $\alpha_v\beta_3$ integrin is added a signal is generated (FIG. 11). Note that even though the concentration of the protein is 100× that used to generate the signals shown in FIG. 9B, there is essentially no background current, only the fluctuating current component (of about 0.2 nA in this case). This is because there is room for only one molecule at a time in the device, and this confirms that, in some embodiments, the background current arises from adsorption of many molecules.

Figure 12:
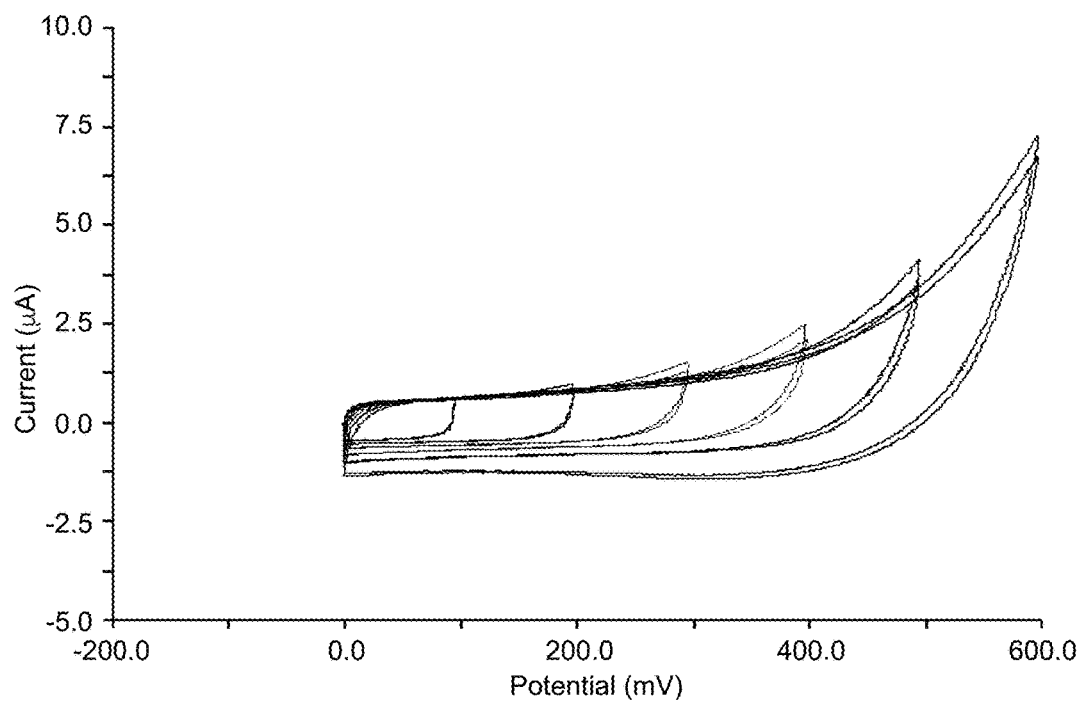
FIG. 12 illustrates cyclic voltammetry of a palladium electrode of a device according to some embodiments of the present disclosure functionalized with cyclic RGD peptide and exposed to a $\alpha_V\beta_3$ integrin solution. Scale is millivolts relative to a silver wire quasi reference.

Stable operation of the device requires control of the operating potential as described for similar devices in PCT publication no. WO2015/130781, entitled, "Methods, Apparatuses and Systems for Stabilizing Nano-Electronic Devices in Contact with Solutions", the entire disclosure of which is herein incorporated by reference. FIG. 12 shows cyclic voltamograms taken with an RGD functionalized palladium electrode in the presence of a solution of $\alpha_v\beta_3$ integrin. As shown, Faradaic current begins to rise above about 400 mV (with respect to a silver wire quasi reference electrode). Since, this is the upper limit of the bias applied to the across the electrode gap, the device operates stably if one electrode is connected to a silver wire (or Ag/AgCl) reference and the other electrode is kept below +400 mV with respect to the reference.

In experiments, the concentration used to obtain signals with the single molecule capture device had to be quite high (i.e., nanomolar or higher) in order for the probability of capturing a single molecule in a reasonable time to be significant. In some embodiments, this probability is proportional to the volume from which molecules can be captured in a reasonable time. For example, if the molecules diffuse freely with a diffusion constant D (e.g., about $10^{-11}$ $m^2/s$), then the volume from which molecules can be collected in a time t, over a linear junction length L, is given approximately by $\pi r^2 L$ where $r^2=Dt$. Taking t=60 s and L=36 nm (approximately the length of the junction around the edge of a 12 nm diameter pore), about 40 molecules would be present at 1 nM concentration in the resulting volume of $6.5\times10^{-17}$ $m^3$ ($=6.5\times10^{-14}$ liters). Referring to FIG. 7, if the junction length, X, is greatly increased (over the value of L given for the perimeter of a nanopore earlier, L=36 nm in the example given) then correspondingly, the sensitivity of the device will also increase. Thus, for a device with X=10 µm, the capture volume in 1 minute capture time becomes $10^{-14}$ $m^3$ or almost 100× greater. Thus, signals are readily obtained at 1 pM concentrations as shown in FIG. 9B. In fact, upon the solution being flowed over the device, the effective capture length is orders of magnitude greater. For the cyclic RGD peptide, capturing $\alpha_v\beta_3$ integrin, the binding process appears to be almost irreversible, so essentially all of the molecules within a capture radius can be swept up. Thus, if about a linear cm of fluid is flowed past a junction slowly enough that each volume of length equal to the junction length spends about a minute over the junction, then concentrations as small as a femtomole will yield a signal.

Figure 13:
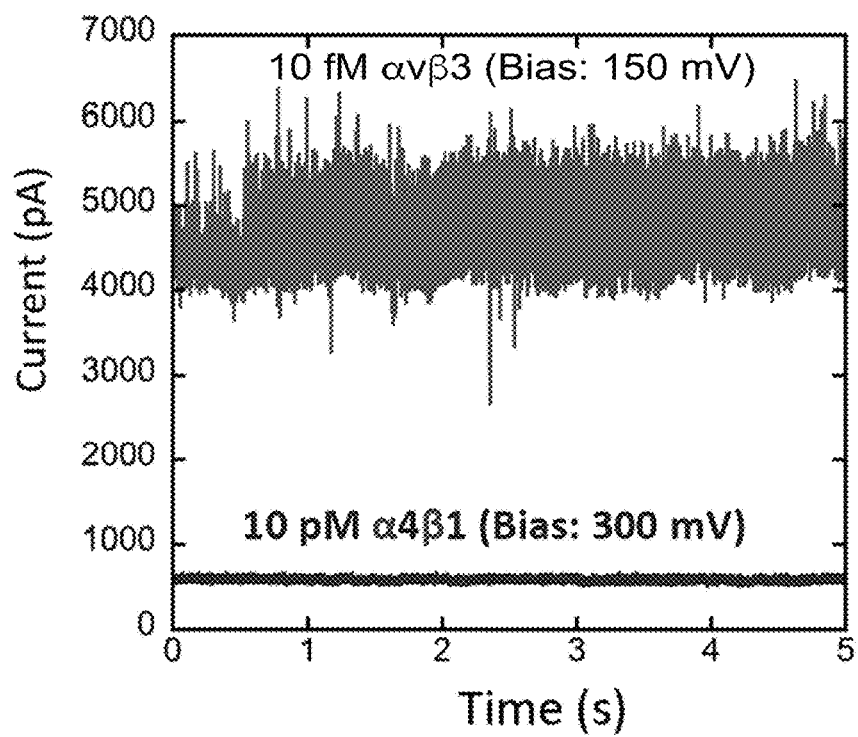
FIG. 13 illustrates output of a device according to some embodiments with a large (micron sized) junction length exposed to a 10 pM solution of $\alpha_4\beta_1$ integrin (lower trace) followed by a 10 femtomolar solution of $\alpha_V\beta_3$ integrin (upper trace).

FIG. 13 shows an experiment in which a 10 pM solution of $\alpha_4\beta_1$ integrin was flowed over large (X=0.1 μm junction) for several minutes with no signal being produced. When 10 fM of $\alpha_v\beta_3$ integrin was introduced, a large signal appeared after a few minutes, which substantially exceeds the sensitivity estimated above (where much longer exposure times would be required for the even larger (X=10 μm) junction geometry.

One of skill in the art recognizes that the specific dimensions given here are exemplary only. For example, a much larger gap (e.g., 5 to 15 nm), can be used if the recognition molecules (cognate ligands) are full sized antibodies (e.g., about 10 nm in extent), so the gap size (d in FIG. 7) would be, for example, 20 nm. An alternative to antibodies could be single-domain antibodies such as those produced by Abcore Inc. (for example). Such single-domain antibodies include molecular weights of 50 kD and linear dimensions of around 2.5 nm, so gaps of 5 nm would be appropriate.

Example 2

Observation of Giant Conductance Fluctuations in a Protein

Proteins are insulating molecular solids, yet even those containing easily reduced or oxidized centers can have single-molecule electronic conductances that are too large to account for with conventional transport theories. Here, the observation of remarkably high electronic conductance events in an electrochemically-inactive protein, the ~200 kD $\alpha_v\beta_3$ extracelluar domain of human integrin is reported. Large current pulses (up to nAs) were observed for long durations (many ms corresponding to many pC of charge transfer) at large gap (>5 nm) distances in an STM when the protein was bound specifically by a small peptide ligand attached to the electrodes. The effect is greatly reduced when a homologous, weakly-binding protein ($\alpha_4\beta_1$) is used as a control. The time- and voltage-dependence of the single-molecule conductance were explored by trapping the protein in fixed-gap (5 nm) tunneling junction devices. Transitions to a high conductance (~nS) state are transient, the protein being "on" for times from ms to tenths of a second, and the high-conductance states only occur above ~100mV applied bias. Thus, these high-conductance states are a non-equilibrium property of the protein. Nanoamp two-level signals indicate the specific capture of a single molecule in an electrode gap functionalized with the ligand. This offers a new approach to the label-free electronic detection of single protein molecules. Electronic structure calculations yield a distribution of energy level spacings that is consistent with a recently proposed quantum-critical state for proteins, in which small fluctuations can drive transitions between localized and band-like electronic states.

Provided herein are direct measurements of the conductance of a large, electrochemically-inert protein (ca. 10 nm diameter) using both STM and a fixed gap device to explore long-range transport. A ~200 kD protein was chosen, the $\alpha_v\beta_3$ extracelluar domain of human integrin because it is electrochemically inert and binds a small cyclic (RGD) peptide selectively. By modifying electrodes with a cyclic RGD containing a cysteine, the attachment point of the protein as well as retarding the denaturation often observed when proteins bind bare electrodes are controlled. This scheme also allows us to use a similar protein ($\alpha_1\beta_4$ that does not bind RGD so strongly) as a control. STM break-junction measurements show current peaks in excess of a nA at gap distances in excess of 5 nm. The time- and voltage dependence of these high-conductance states were explored using a multilayer edge molecular electronic device (MEMED) consisting of a sandwich of two Pd layers separated by a layer of $Al_2O_3$ dielectric deposited by atomic layer deposition (ALD) to a thickness of 4 to 5 nm. Motivated by evidence for quantum coherent effects in proteins were carried out electronic structure calculations to compare the distribution of energy levels to the predictions of an analysis based on quantum-critical states in proteins.

STM Break Junction Measurements

Figure 14A:
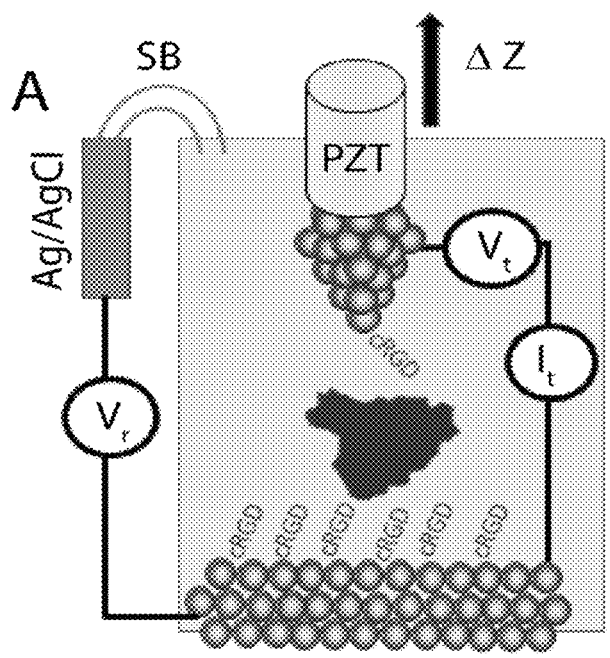
FIGS. 14A-14E are STM current-distance traces showing large current peaks at large distances when integrin protein binds specifically to an electrode.
Figure 14B:
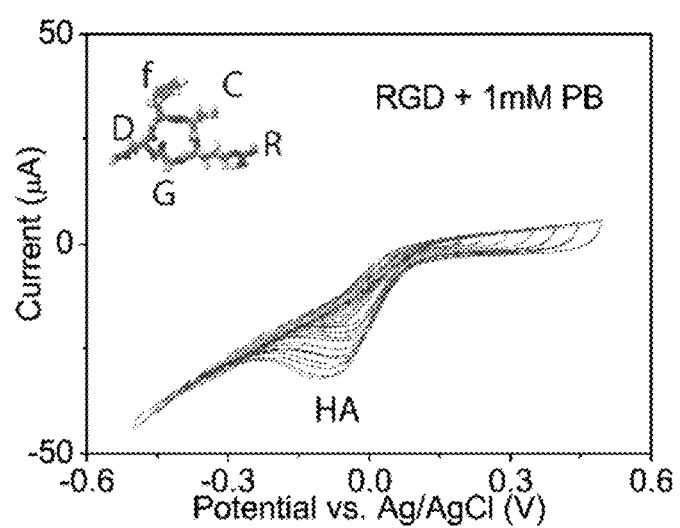
Figure 14C:
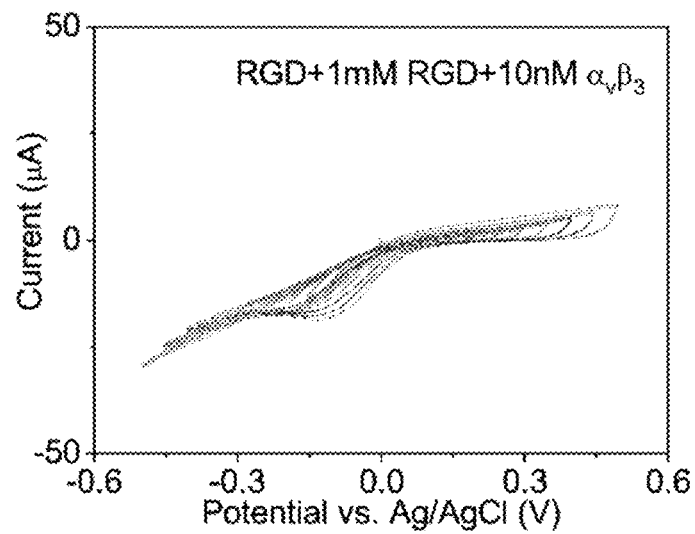
Figure 14D:
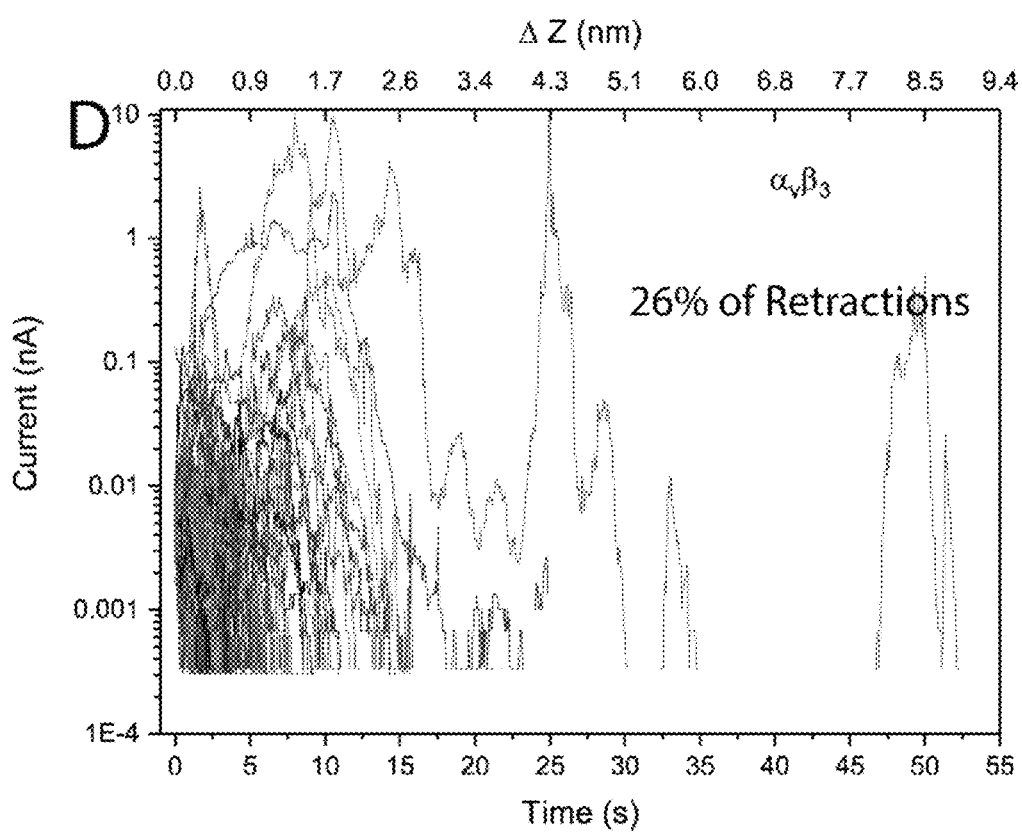
Figure 14E:
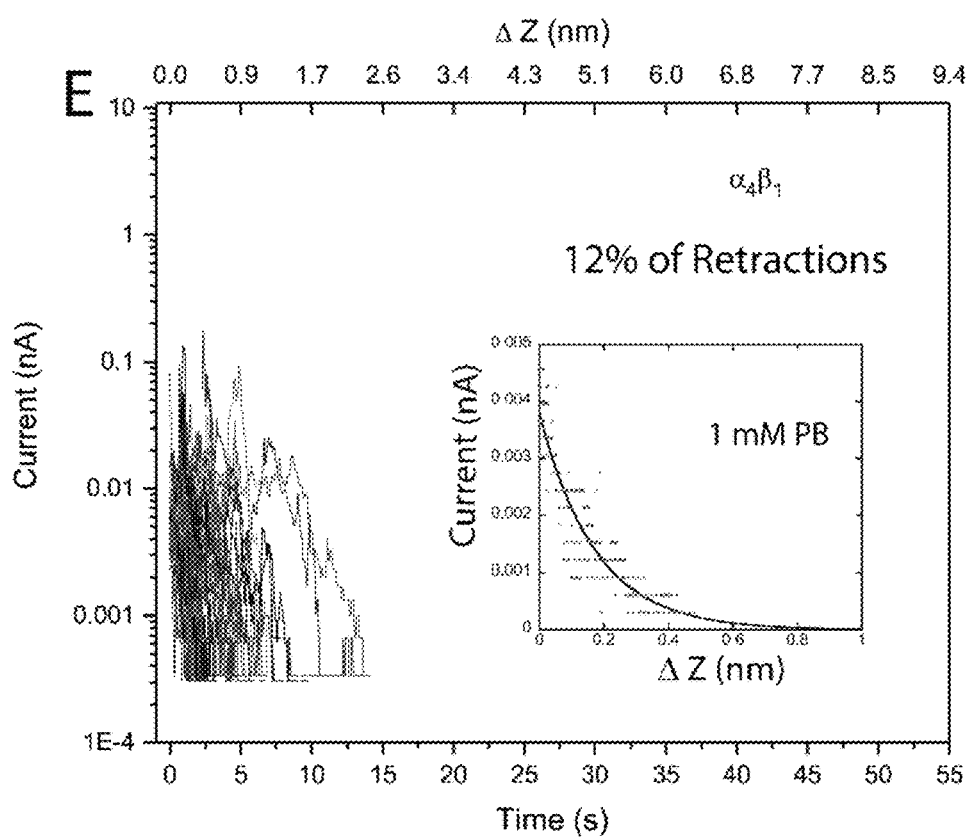
Figure 15A:
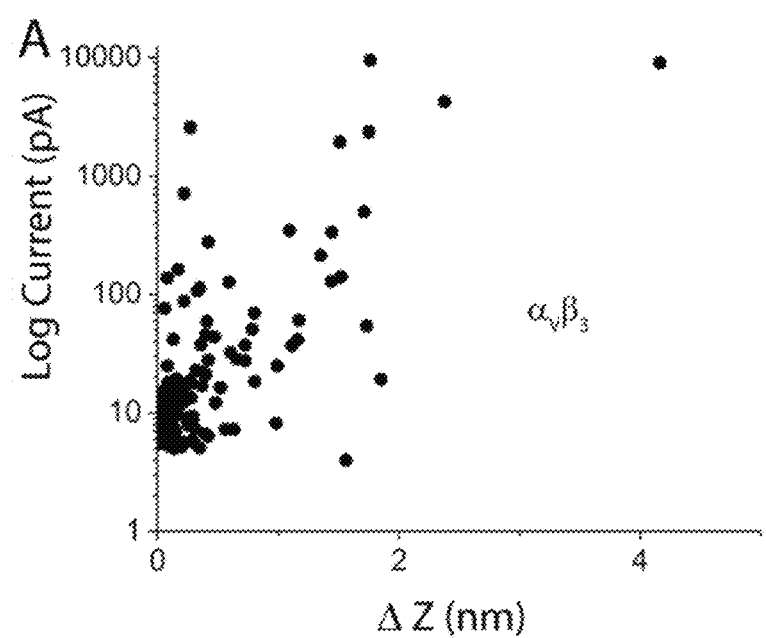
FIGS. 15A-15C show summary of current peaks observed in STM retractions. Scatter plots of logarithm of peak current vs. retraction distance (i.e., from the initial set-point gap of about 2 nm to the current peak) for $\alpha_V\beta_3$ (FIG. 15A) and $\alpha_4\beta_1$ (FIG. 15B).
Figure 15B:
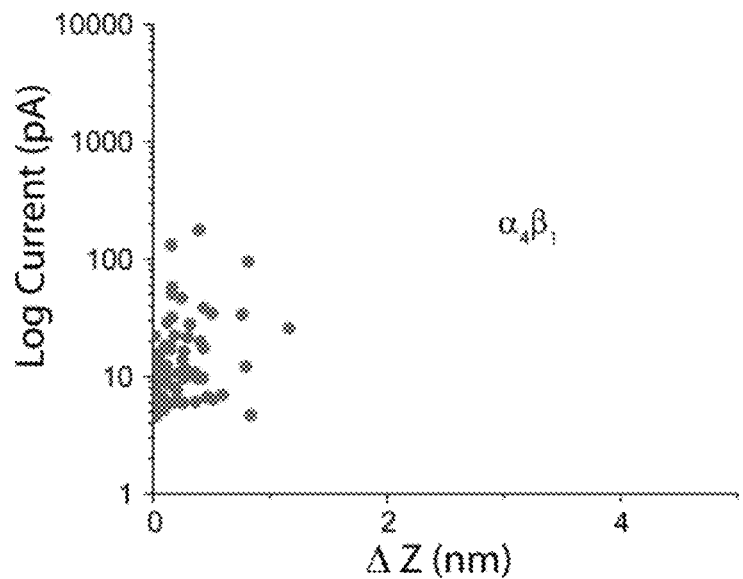

FIG. 14A shows a schematic layout of the STM break-junction measurement. A Pd wire probe, etched to a sharp point and insulated to within a few hundred nm of its apex was used in an Agilent PicoSPM together with a Pd-coated substrate as described elsewhere. Pd, rather than Au was used because tunneling devices made with Pd are more stable. Probes and substrates were functionalized with cyclic RGD peptide (inset FIG. 14B) as described in Methods. Measurements were carried out in 1 mM phosphate buffer (pH=7.4) with the potential of the substrate controlled at a voltage $V_r$ with respect to an Ag/AgCl reference. The reference electrode was connected to the measurement cell via a salt-bridge (SB) because it was found that adsorption of protein onto the surface of a simple silver-wire quasi reference resulted in instabilities in the reference potential. Integrin itself is electrochemically-inert, but the Pd surface has a rich electrochemistry. Cyclic voltammetry of a Pd surface functionalized with cyclic RGD peptide is shown in FIG. 14B, where a prominent cathodic peak ("HA") is associated with hydrogen adsorption. Addition of $\alpha_v\beta_3$ protein blocks access to the surface, resulting in ~30% reduction in the cathodic peak (from 1.3 to 0.9 $C/cm^2$), showing that the integrin is electrochemically inactive in this potential range. In order to avoid both this cathodic peak and the onset of Pd oxidation at positive potentials, both electrodes were kept at potentials between 0 and 0.5V vs Ag/AgCl. The STM gap was set to an initial current of 4 pA (13 pS conductance at $V_t$=0.2V, corresponding to a distance, $Z_0$, of about 2 nm) and the probe was then slowly (0.17 nm/s) retracted. The tunnel current decayed rapidly (~0.2 nm decay length—inset in FIG. 14E) in buffer alone. However, when $\alpha_v\beta_3$ protein was added to a final concentration of 10 nM, remarkably large current spikes were observed at retraction distances up to $\Delta Z$=3 nm (overall gap, $Z_0+\Delta Z$~5 nm) as shown in FIG. 14D. When the experiments were repeated with $\alpha_1\beta_4$ protein substituted for $\alpha_v\beta_3$, the event frequency dropped from 25% of all retractions to 12%, and peak currents and values of $\Delta Z$ were significantly reduced (FIG. 14E). Summaries of combined measurements from four separate experiments with each protein are shown in FIGS. 15A and 15B. Many current points for $\alpha_v\beta_3$, exceed 0.1 nA (i.e., conductances >0.5 nS) at distances $Z_0+\Delta Z$>3 nm (FIG. 15A). Clearly these currents cannot arise from a tunneling process with $\beta$~0.87 $Å^{-1}$ for which $G_0 \cdot e^{-\beta x}$ yields values smaller than $10^{-16}$ S.

The charge transferred in these events (obtained by integrating the current peaks) spans a large range of values (FIG. 15C), but even the smallest (Q~1pC) correspond to transfer of about $10^7$ electrons, a charge too big to be explained by polarization events on this length scale.

Table 1 summarizes the frequency with which these large current pulses are observed in STM measurements, showing also the effect of increasing bias. Large current events are barely seen below 0.1V, their frequency rising with increasing bias above this threshold. The experiments were repeated without a reference electrode, finding essentially identical results over the range of 0.1 to 0.5V (Table 1) presumably because the large-area substrate used in the STM experiments serves to stabilize surface potential somewhat. The existence of a threshold bias, below which these high-conductance states do not occur, implies that they are not an equilibrium property of the protein.

TABLE 1

| Bias | 0.5 V | 0.5 V | 0.2 V | 0.2 V | 0.1 V | 0.1 V |
|---|---|---|---|---|---|---|
| Reference | None | Ag/AgCl | None | Ag/AgCl | None | Ag/AgCl |
| $\alpha_4\beta_1$ | 0.24 (0) | 0.3 (0.01) | 0.12 (0) | 0.15 (0) | 0 | 0.01 |
|  | N = 133 | N = 99 | N = 144 | N = 74 | N = 87 | N = 91 |
| $\alpha_v\beta_3$ | 0.56 (0.09) | 0.58 (0.2) | 0.26 (0.03) | 0.32 (0.01) | 0.06(0) | 0.07(0) |
|  | N = 137 | N = 100 | N = 136 | N = 75 | N = 84 | N = 96 |

In Table 1, fraction of retractions that showed large current events for three values of the probe bias with the substrate either floating with respect to the solution (Reference="None") or at 0V vs Ag/AgCl (Reference ="Ag/AgCl"). The fraction in parenthesis corresponds to events that overflowed the current limit of the amplifier (11 nA). 0.5V bias approaches the potential for surface oxide formation of the Pd, but no significant oxidation currents were observed.

The molecular specificity of the $\alpha_V\beta_3$-RGD binding was investigated by comparing the selectivity of RGD functionalized surfaces with the selectivity of surfaces functionalized with cyclic RGE, a cyclic peptide of the same charge (RGD, pI=6.09; RGE pI=6.18) and differing by only one carbon atom. The effects of functionalizing only the probe or substrate were also investigated. The results of these experiments are summarized in Table 2 (no events were observed without functionalization). Essentially the same frequency of events was observed with only one electrode functionalized as with both, consistent with the known single binding site for RGD peptide. Significantly more selectivity was obtained with RGD peptide than with RGE ("Ratio" column in Table 2). It can be concluded that one chemical contact is required for the high conductance to be observed, and that the specificity and frequency of events increases with the chemical specificity of the contact. In addition, specific binding results in larger current peaks at larger retraction distances than obtained with less-specific binding. The peptide coating probably retards the denaturation often observed when proteins bind bare electrodes, as suggested by the specificity of the binding.

TABLE 2

| Ligand | Modification | $\alpha_4\beta_1$ | $\alpha_v\beta_3$ | Ratio |
|---|---|---|---|---|
| RGD | Tip + Substrate | 0.19 | 0.57 | 3.1 |
|  | Tip only | 0.21 | 0.55 | 2.6 |
| RGE | Tip + Substrate | 0.25 | 0.31 | 1.2 |
|  | Tip only | 0.28 | 0.36 | 1.3 |
| None |  | 0 | 0 | NA |

Table 2 shows effect of electrode modification on the frequency of large current events. RGE is a cyclic peptide differing from RGD by only one carbon atom.

Fixed Gap Device Measurements

Figure 16A:
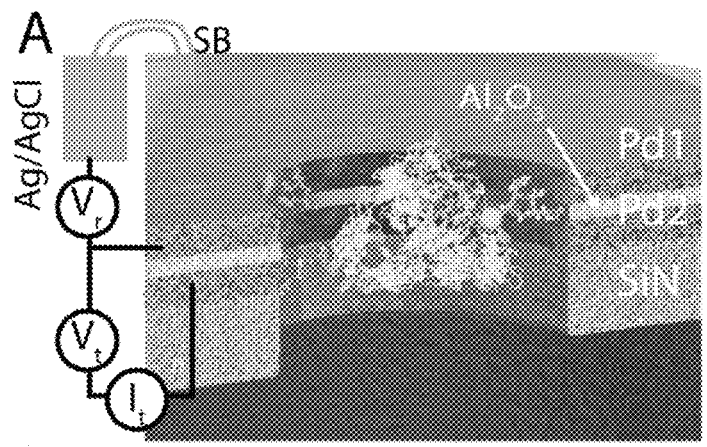
FIGS. 16A-16I show fabrication of the fixed-gap tunnel chip and some typical results at a bias of 300 mV.
Figure 16B:
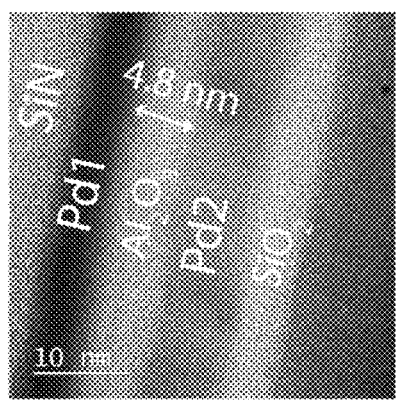
Figure 16C:
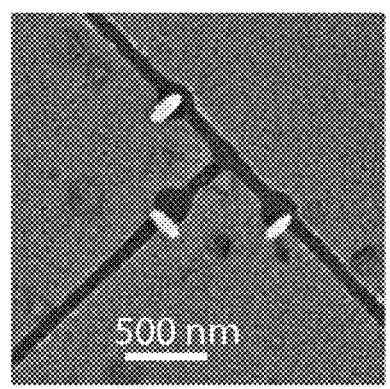

A fixed gap tunneling device has significant advantages over STM measurements. These are: (1) The gap does not change with electrical operating conditions, so that the bias may be changed without changing the gap; (2) The gap may be determined with some precision by TEM measurements; (3) The device is much smaller, so the associated electrode capacitances are smaller and the corresponding frequency response is higher. The layout of our MEMED is shown in FIG. 16A. It is fabricated much as described in our earlier paper. The basic fabrication of the layered device (10 nm Pd, 4 to 5 nm $Al_2O_3$ followed by 10 nm Pd, resting on top of a 25 nm SiN substrate and passivated on top with $SiO_2$) was carried out by Norcada Inc. (Edmonton, Alberta). A TEM image of a cross section of the junction (cut out using a focused ion beam mill) is shown in FIG. 16B. Our original devices had large (micron-scale) openings, but it was desired to restrict the region over which proteins could be captured to dimensions small enough that the capture of multiple molecules in the tunnel junction was unlikely (illustrated schematically by the capture of a single integrin in FIG. 16A). RIE was used to thin the underlying SiN substrate to ~15 nm, followed by e-beam lithography using a hard mask and further RIE etching (FIG. 16C and Methods). In this way, slits were produced that were 50 to 100 nm across and up to 400 nm long, though the active area was defined by the top electrode widths of about 100 nm (FIG. 16C). After cleaning and functionalization (Methods) the device was immersed in 1 mM phosphate buffer (pH=7.4) with the electrode potentials controlled with respect to an Ag/AgCl electrode coupled via a salt bridge (SB in FIG. 16A). Potential control is more important for small-area junction devices because the area of the electrodes exposed to the electric double layer is minute ($\sim 10^{-15}$ m$^2$) so that small changes in interfacial charge can change the surface potential significantly (In contrast to the STM where a macroscopic substrate stabilizes the potential).

Figure 16D:
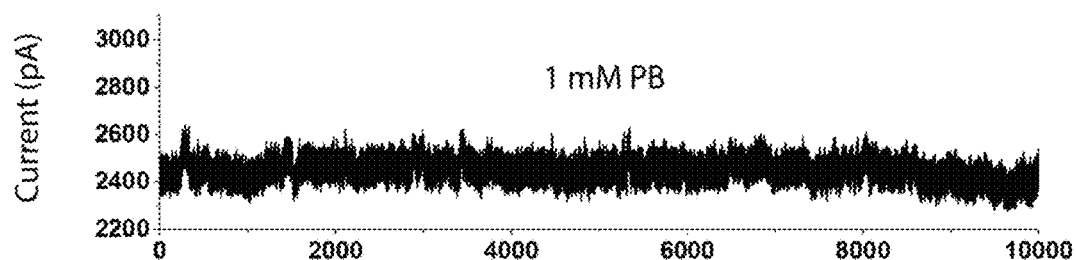
Figure 16E:
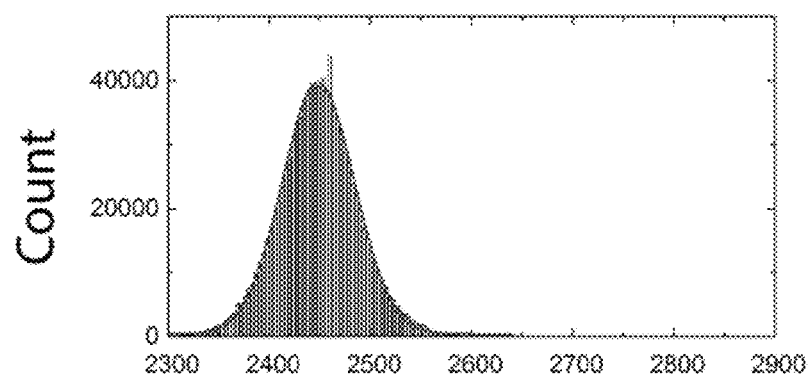
Figure 16F:
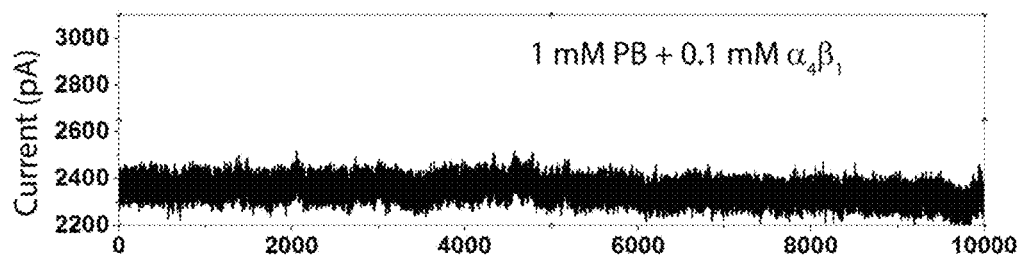
Figure 16G:
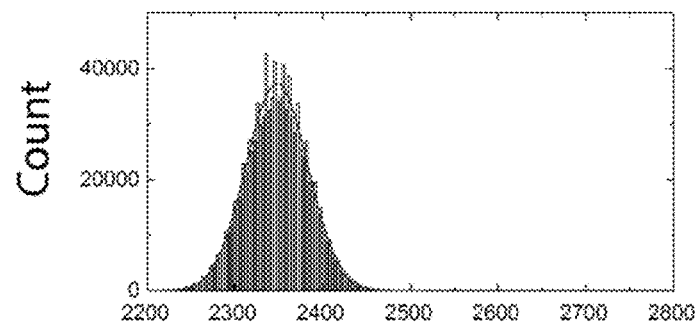
Figure 16H:
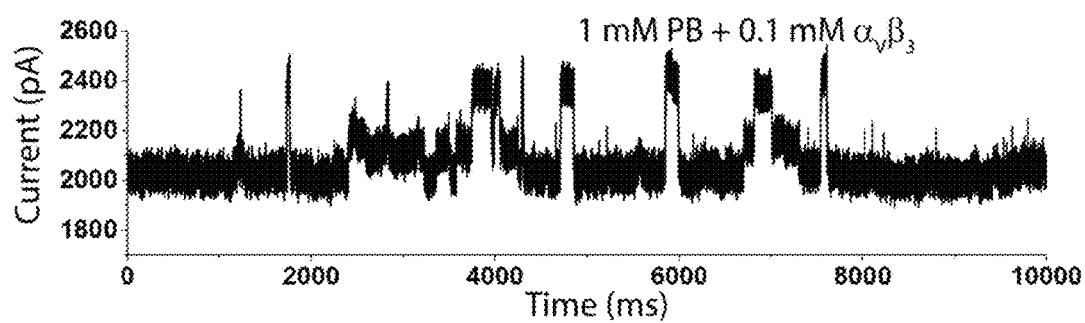
Figure 16I:
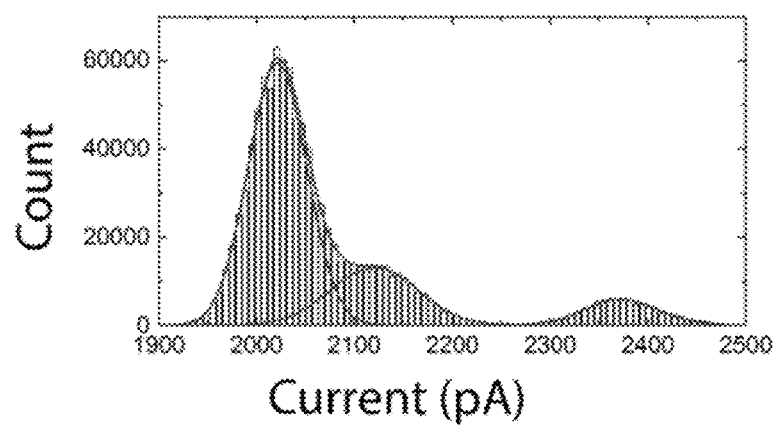

Our devices often suffer from failure of the passivation layer ($SiO_2$ in FIG. 16B) so that, even in the dilute electrolyte, leakage currents can be substantial (e.g., a few nA, FIG. 16D). Control experiments show that these currents are essentially the same when measured between any one of the tunneling electrodes and a reference electrode in solution, and that they increase as damage to the top passivation layer becomes more obvious. Thus, these are currents that pass from exposed regions of the top electrodes via the electrolyte, and they are not a consequence of tunneling or electrochemical leakage across the tunnel gap itself. These leakage currents (FIG. 16D) show no distinctive features beyond the shot- and system electronic noise (distributed as a Gaussian, FIG. 16E). When 100 mM $\alpha_1\beta_4$ protein was added (FIG. 16F) the background current falls a little, presumably because of passivation of the exposed electrodes by non-specific adsorption of this protein. Once again, the signal is featureless, displaying the same intrinsic noise as observed in buffer alone (FIG. 16G). (In contrast to the STM measurements, no features have been observed in the fixed-gap devices in any measurement taken in the presence of $\alpha_1\beta_4$.) However, once $\alpha_\nu\beta_3$ protein is added to the same device, dramatic jumps occur in the current (FIG. 16H). The background leakage current is reduced by about 20% on addition of the protein, consistent with the passivation effect seen in the macroscopic electrochemical measurements (FIGS. 14B, 14C). The signal jumps up from the baseline to two well defined levels (FIG. 16I) in this case. The states are separated by nearly 0.5 nA, corresponding to ~1.5 nS conductance ($V_t$=0.3V). This is consistent with the surprising result observed in the STM measurements but in a device of a known and fixed 5 nm gap (FIG. 16B). Events like this have been observed in two devices held under potential control, and in three other devices in which potential was not controlled but very similar behavior was observed. In order to eliminate the possibility that the signal comes from a damaged region of the junction that might be small enough to sustain conventional tunnel currents, sample chips from each wafer were tested with the chemistry previously used for tunneling detection of DNA nucleotides, obtaining no signals at all.

Figure 17A:
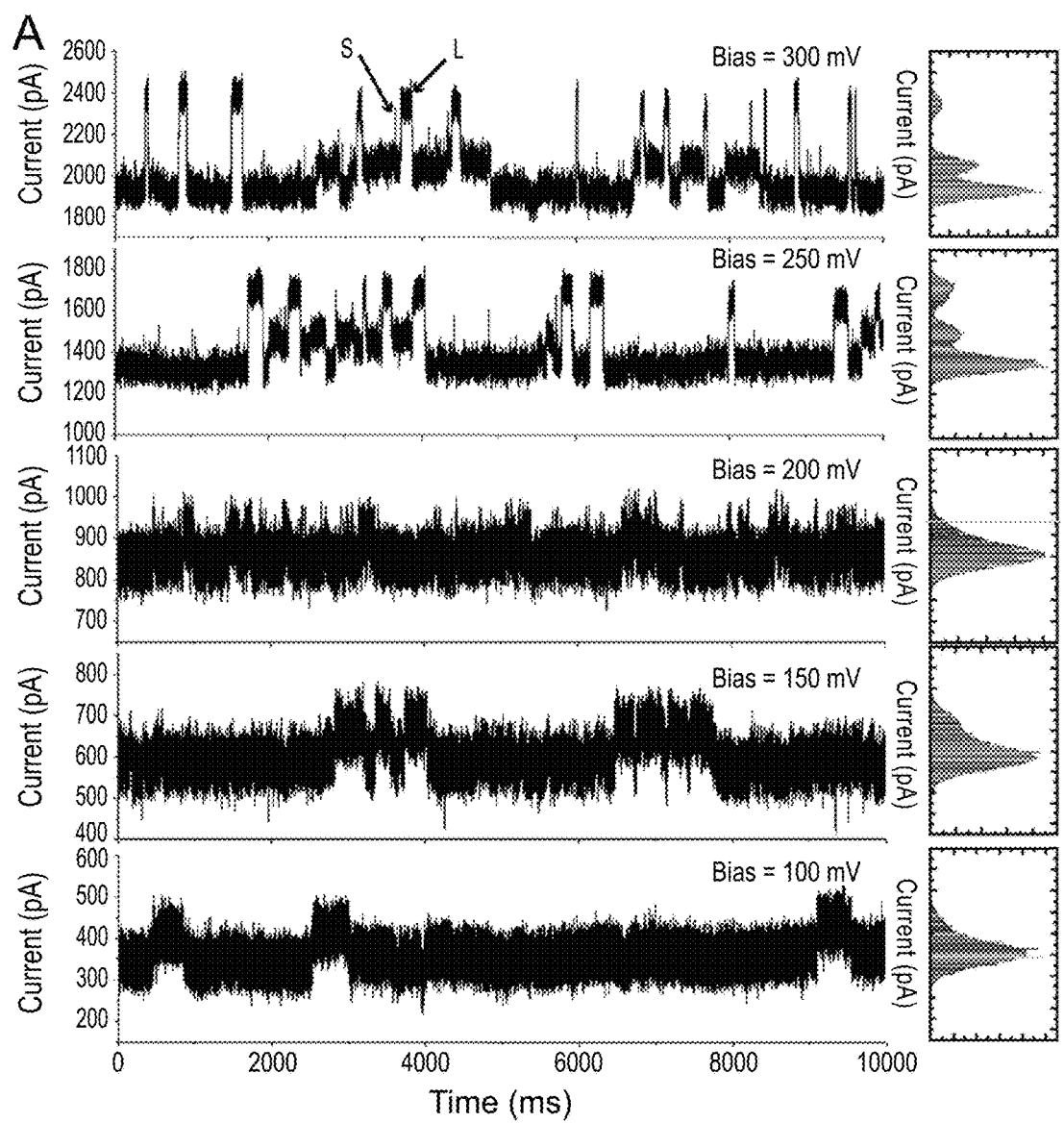
FIGS. 17A-17C show bias dependence of chip-signals from $\alpha_V\beta_3$ protein.

A series of current-time traces taken at biases from $V_t$=100 mV to 300 mV ($V_r$=0) are shown in FIG. 17A. Below $V_t$=100mV no features are observed and the traces have an identical noise distribution to the controls (FIGS. 16D-16G). At 100 mV, jumps in current start to occur. These are quite similar over periods of many seconds and give rise to a distinctive "bump" in the amplitude distribution (see the histogram to the right of the trace). Such two-level signals (2LS) are indicative of a single switching event, therefore most likely of the binding of a single molecule. As the bias is increased, both the amplitude and frequency of switching events increases, with a transition (in this case) to three-level signals (observed at $V_t$=250 and 300 mV). The slits are big enough to capture more than one integrin, so the possibility that signals with more than two levels reflect the simultaneous binding of more than one molecule cannot be ruled out.

Figure 17B:
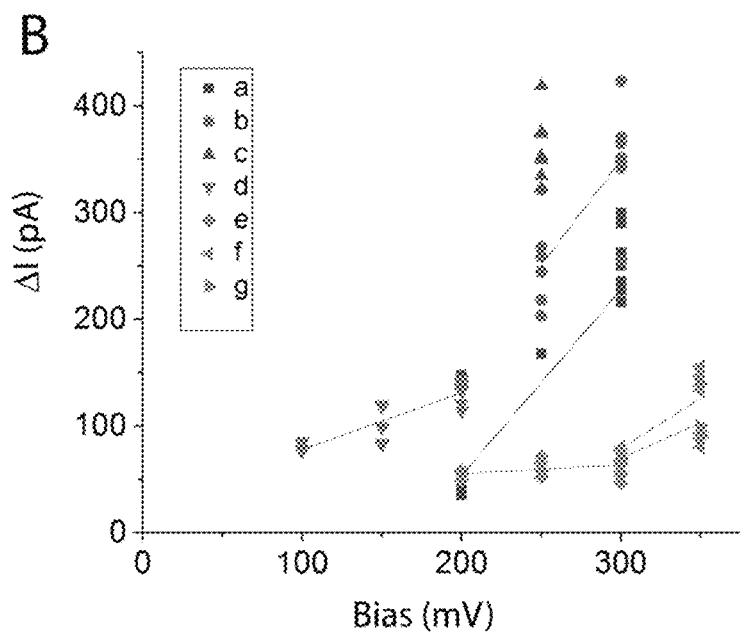

The traces shown in FIG. 17A span 10s, over which time the signals appear quite uniform. The current distributions can change significantly over longer times. Accordingly, each stable run of signal separately for two devices at two reference potentials have been analyzed with the results summarized in FIG. 17B. The vertical spread of data represented by the same symbol at the same bias gives a measure of the change of signal amplitude from one burst of 2LS signal to another, and could represent changes in the binding of a given molecule, or the capture of an entirely different molecule. In cases where three (or in one case four) levels appeared, they are analyzed separately and the current jumps referred to as peak 1 (2LS), peak 2 (3 LS) and peak 3 (4LS) in the caption of FIGS. 17A-17C. The first noticeable feature is that, in contrast to the STM data (where the gap was changed continuously) the distribution of switching currents is remarkably narrow (a factor of four at most in a given set of conditions). The switching currents all increase with bias, but with a ~0.1V threshold for the onset of signals (as was observed with the STM measurements). The "on" state conductances are all on the order of 0.1 nS, quite a surprising result given that one of the two electrodes must contact the protein by means of a non-specific interaction that could be quite variable. The second feature of these data is the significant differences between different chips (e.g.,  traces f and g vs. traces a-d). Repeat runs with a given chip overlap somewhat (e.g., a and d, and f and g) though a given chip can change significantly in slightly different experimental conditions (c.f., a and e). Linear fits to runs a,b, f and g intercept the zero current axis between 120 to 200 mV, consistent with the observed threshold for the onset of signals. Linear fits to data sets d and e have a much smaller slope, but once again, no signals were observed below 0.1V.

Figure 15C:
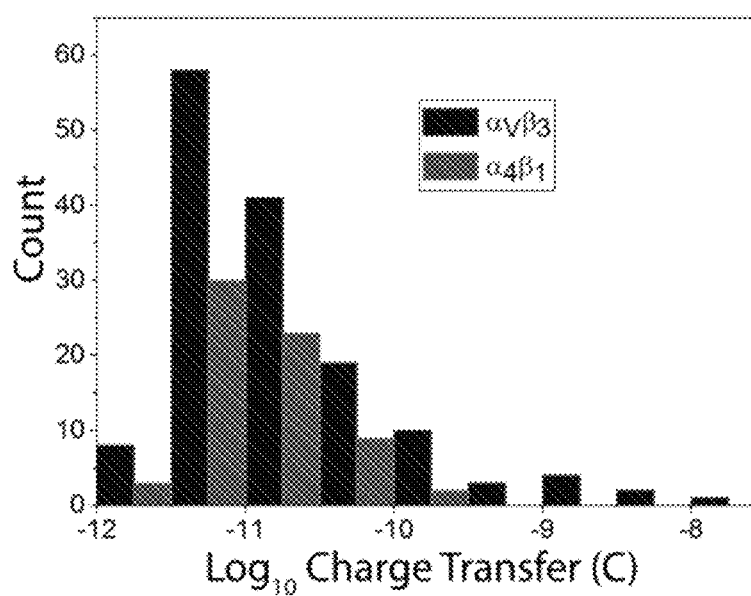
Figure 17C:
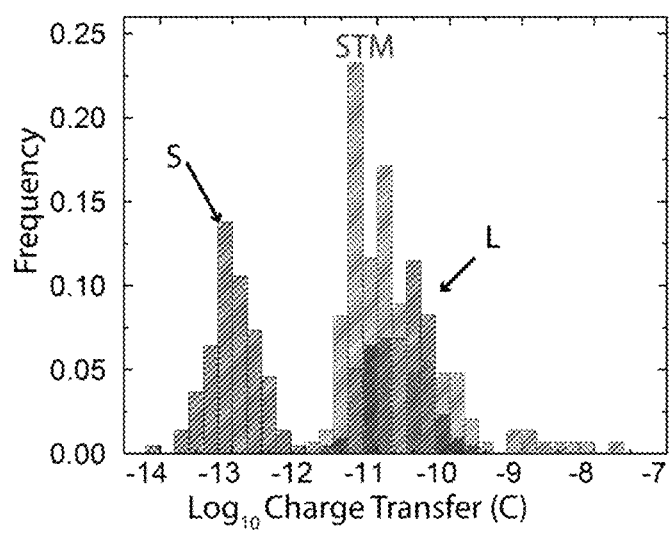
Figure 18A:
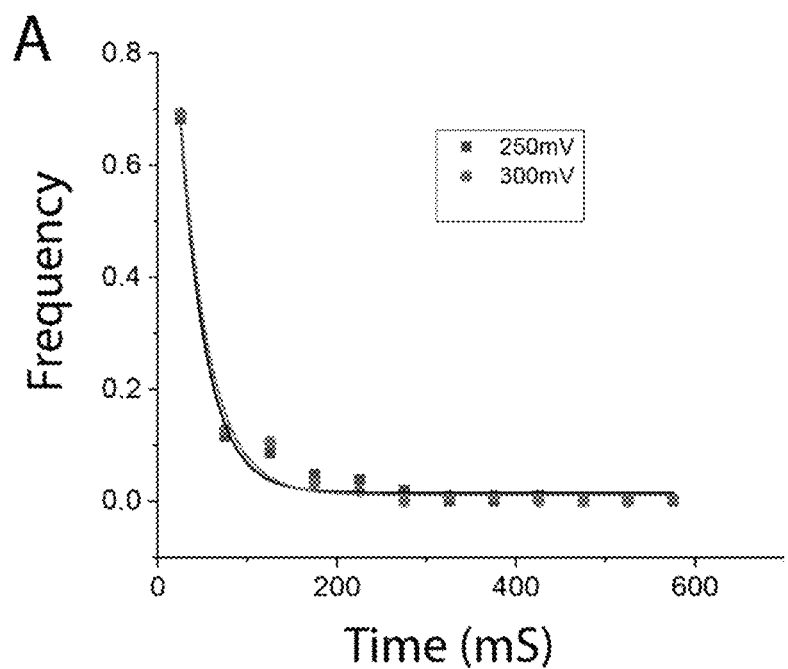
FIGS. 18A-18D show time structure of the current fluctuations.
Figure 18B:
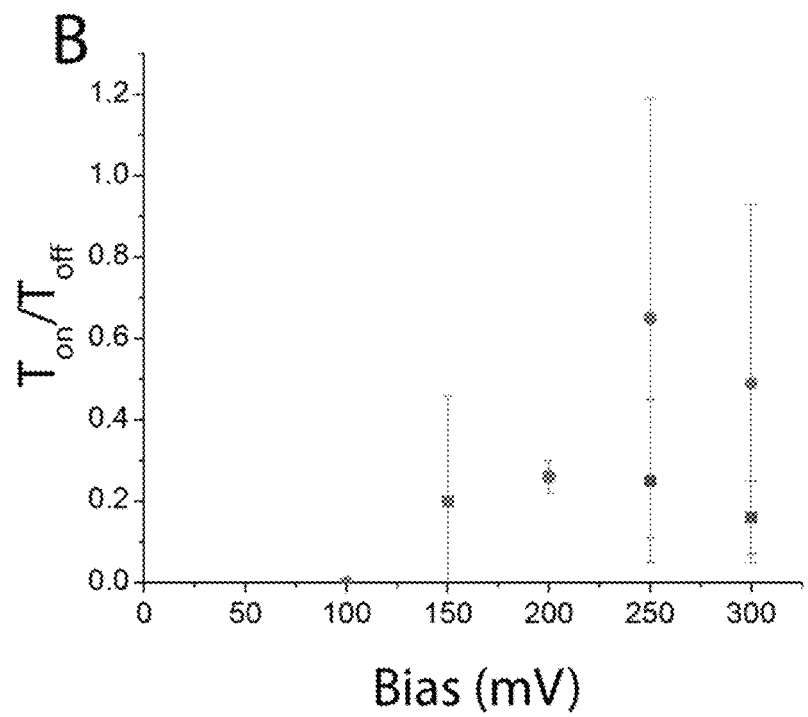
Figure 18C:
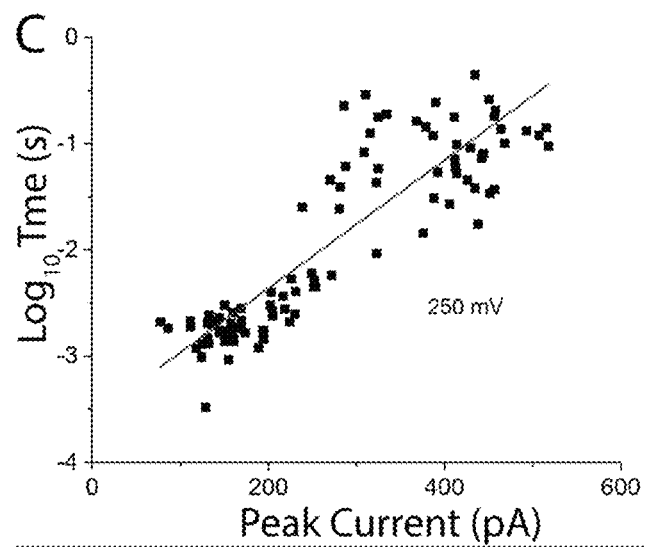
Figure 18D:
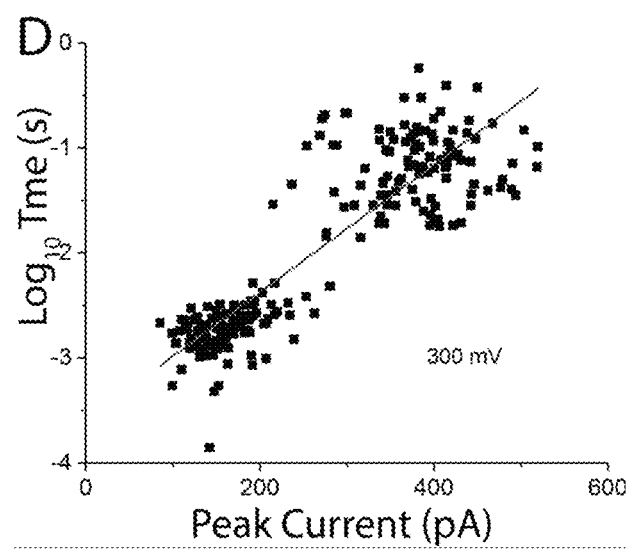

In contrast to the limited range of measured current jumps, there is an enormous variation in charge transferred (FIG. 17C) during each on-state. Many of the events overlap the distribution observed in STM measurements (FIG. 15C, data overlaid on FIG. 17C). In addition to the long-lived "on" states observed in the STM, the improved frequency response in these small devices reveals a population of fast events. A fast event is labeled "S" in FIG. 17A, with the corresponding charge transfers labeled "S" in FIG. 17C. The distribution for the longer-lived events is labeled "L" in FIG. 17C with a typical corresponding pulse labeled "L" in FIG. 17A. In these time resolved measurements it is clear that the wide distribution for the values of charge transferred is a consequence of the large spread of "on" times (FIGS. 18C, 18D). The short-time distribution of "on" times is exponential and does not change significantly with bias, with a mean time of 31±2 ms (FIG. 18A). The ratio of the total "on" time to the total "off time" can be calculated from the number of points under the upper level peaks divided by the number of points in the baseline peak in the amplitude histograms for each run of 2LS signal (examples of these histograms are given to the right of FIG. 17A). A plot of the means of these "on" to "off" ratios is shown in FIG. 18B (where the error bars are ±1 sd of the distribution of values at any one bias). The bias threshold of about 100 mV is clear, and the fraction of on-time increase roughly linearly with increasing bias.

A linear plot of decay times fails to capture the full range of events, so scatter plots of current vs. logarithm of the on-time for each event are presented in FIGS. 18C and 18D. On this logarithmic display, they show the clustering of times that gives rise to the two distinct peaks in the histogram of log(Q) (FIG. 17C). These plots also show that the on-currents are linearly related to the logarithm of the on-times for each event.

Discussion and Conclusions

A large, electrochemically inert protein can carry currents of nearly a nanoamp under a bias of a few tenths of a volt for times that can approach a tenth of a second, and over distances between electrodes of 5 nm or so. This effect appears only above a threshold bias of about a tenth of a volt, and the observed currents fluctuate on and off on ms to 0.1s time scales. The log of the "on-time" is linearly related to the observed peak current and the overall time in the conducting state increases as bias is increased. Much of the fluctuating current is a two-level signal. Taken together with repeated observations in gaps small enough to accommodate only a few (1 to 10 molecules) it is concluded that the 2LS signals originate with a single molecule, likely explaining the rather reproducible current-switching levels observed at a given bias. Signals with multiple levels are larger, suggesting that they may reflect contributions from more than one molecule trapped in the gap. Finally, the signals are sensitive to the nature of the chemical tether used to link the protein to one of the electrodes. Events are more frequent with a specific (RGD) tether and its specific target ($\alpha_\nu\beta_3$) than with an off target protein ($\alpha_4\beta_1$) or a less selective tether (RGE). This observation is useful, in as much as it demonstrates that the proteins on the electrode are close enough to their native state for this recognition to occur. It also suggests that artifacts owing to contamination are unlikely to be responsible for these signals. The specific tethering has another important consequence, in that electronic features are enhanced by specific binding, manifested in both greatly increased peak currents, and much larger peak-current distances (FIGS. 15A-15C).

It is clear that these large currents cannot be accounted for by a pure-tunneling mechanism. It is known that high currents (nA) can be measured across large area junctions containing thousands of ferrocenes, but it is not known whether any widely-accepted mechanism for long-distance transfer of large amounts of charge at high (nA) rates over many nm in single molecules that lack redox centers. Some possibilities are examined below.

Mechanisms involving localized intermediates: Long-range transfer of significant charge can occur in the presence of a high density of redox centers, spaced closely enough for coherent overlap to occur. Contacting redox cofactors that are degenerate within the energy range of vibronic broadening can support coherent transport over significant distances via a flickering resonance mechanism. For example, in G-rich DNA where readily oxidized moieties are stacked in close contact, band-like transport can occur over distances of ~1.5 nm. Systems much larger than this would require either significant tunnel transport ($\beta \ll 1$) to couple the delocalized regions, or intermediate redox active centers that store electrons between transport steps (but with a small enough reorganization energy to facilitate rapid redox turnover). Such features seem unlikely in the case of integrin protein.

Small gap electrochemistry: The discussion above is predicated on the macroscopic electrochemical measurements that show significant reduction of voltammometric features when protein is adsorbed onto the electrode surface (FIGS. 14B, 14C). How might the situation change when two electrodes are in close proximity? A redox-active species with fast turn-over kinetics in the gap can generate significant currents by cycling between the electrodes (reduced at one, oxidized at the other) when the electrode potential difference exceeds the formal potential. The resulting current is given approximately by $De/d^2$ where D is the diffusion constant ($5 \times 10^{-6}$ cm$^2$/s for a small ion) and d is the gap. For d=5 nm this is about 3 pA, much smaller than the features observed here. To account for the observed currents one would have to postulate a mechanism that continued to released hundreds or thousands of highly reactive ions, and do so only when the target protein bound specifically.

Yet another possibility is that the presence of the protein enhances the hydrogen adsorption current (HA in FIG. 14B) by facilitating rapid proton transport between the two electrodes. The maximum bulk currents for this effect are ~60 µA/cm$^2$. For an electrode area of 400×10 nm (a maximum area for one of the MEMED electrodes) this would be $10^{-3}$ pA. The protein would have to enhance proton transfer by a factor $10^5$ or more, do so in way that is sensitive to the attachment chemistry, and manage to do this at a potential positive of the observed peak in the cyclic voltammetry. This seems unlikely.

Transient Charging: Could the observed current pulses correspond to transient charging/discharging of ionized groups on the surface of the protein as a consequence of local pH changes near the electrode surface? At pH 7.4, the net charge for $\alpha_v\beta_3$ is $-45.1$e, and $-35.5$e for $\alpha_4\beta_1$ (chargeable groups mainly include R, H, K residues (positive) and D, E residues (negative)). Millions of adsorbed proteins would be required to account for even the smallest charge transfers observed here.

Heating: Is the assumption correct that the protein retains a native structure? Since the mechanism of charge transfer is unknown, it cannot be assumed that is dissipationless (as tunneling is). In the worst case where all the electrical power is dissipated in the protein, P~0.5 nW (1 nA, 0.5V). The temperature rise at the surface of a hollow sphere of radius a immersed in an infinite heat bath of thermal conductivity K (0.6 W/m.K for water) is given by $\Delta T = P/4\pi K a$ giving, for a=5 nm, $\Delta T < 1K$. In practice, the behavior of the junctions is reasonably reproducible (see the discussion above) when the bias is below 0.5V. Thus, thermal denaturation seems unlikely.

Is coherent transport possible? It has recently been proposed that, rather than simply being aperiodic, many functional proteins may have rather special structures that poise them at a critical point (quantum criticality) that lies between the insulating states generated by truly random systems and the conducting states found in metallic systems. In the space of all possible random arrangements, the quantum-critical state is extremely improbable, unless some (unknown) evolutionary pressure led to it. Systems at this point have the property that small fluctuations can push them into either a pure insulating or a pure metallic state. One indication of quantum-criticality is found in the distribution of energy-level spacings for a system. In the case of a metal, levels follow a Gaussian distribution $$P_w(s) = \frac{\pi s}{2} \exp\left(-\frac{\pi s^{-2}}{z}\right). \tag{1}$$

A random-Poisson distribution applies to insulators:

$$P_p(s) = \exp(-s). \tag{2}$$

At the quantum critical point, the distribution becomes a modified Poisson function:

$$P_T(s) = 4s \exp(-2s). \tag{3}$$

Figure 19:
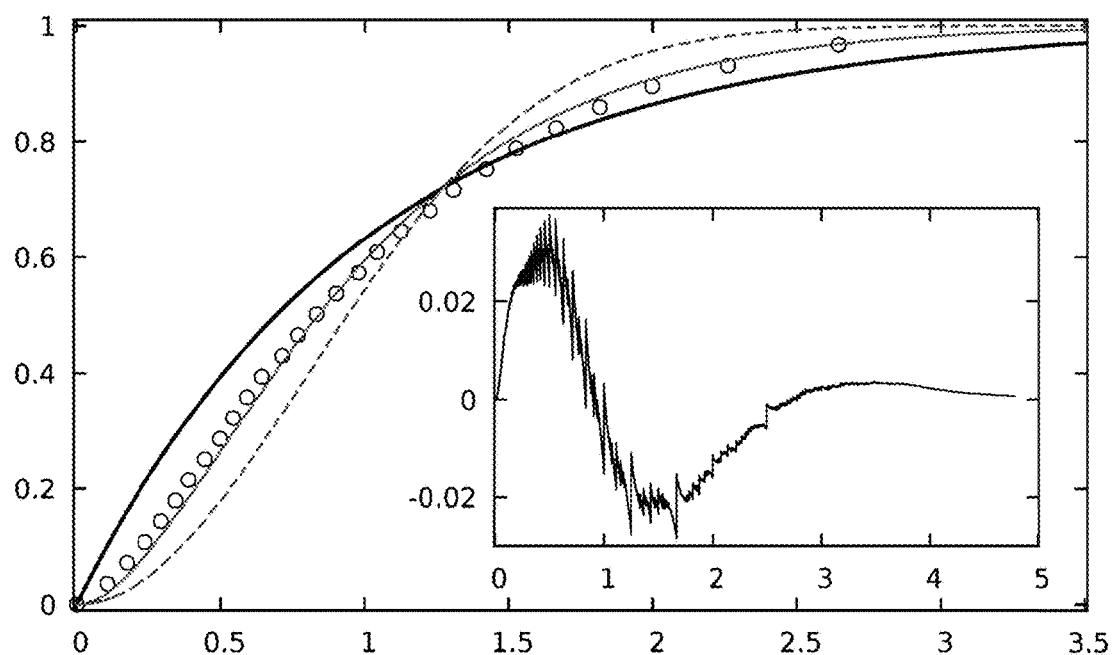
FIG. 19 is a graph showing calculated cumulative level spacing distribution (orange circles) for $\alpha_V\beta_3$ Integrin protein (PDB ID: 4G1M). Only every 2000 value is shown for legibility. For comparison the theoretical curves $I_P$ (s) (black line), $I_W$ (s) (blue line) and $I_T$ (s) (yellow line) are also shown. Inset: Difference between the data curves and $I_T$ (s) are shown. Each value is plotted. The error is below 4% in probability. The calculated distribution is compatible with quantum criticality.

Analysis of a number of conducting polymers and insulators finds that they fit distributions (1) and (2), as expected, whereas many functional proteins fit distribution (3). This is not proof of quantum criticality (nor does it address the equally important question of coherence) but an inquiry at least can be made regarding if the electronic structure of $\alpha_v\beta_3$ protein is consistent with one of these distributions. Accordingly, electronic structure calculations were carried out using the known structure of the hydrated protein (but without including the water molecules: Methods). Cumulative distributions of energy level spacings were used because these avoid binning artifacts. The results are summarized in FIG. 19 (orange circles) together with the cumulative distributions corresponding to the three distribution functions listed. The calculated points lie on the quantum critical distribution (Equation 3). Thus, the possibility that collective quantum effects playing a role cannot be eliminated The nature of the conducting state, charge injection into the state, and the mechanism whereby a local field might drive the transition remain obscure.

Origin of the fluctuations: Assuming that an external field could indeed drive a protein into a conducting state, can an inquiry be made on the subsequent fluctuations? Such fluctuations are reminiscent of the "contact" fluctuations observed in many molecular junctions. If, indeed, the protein is driven into a long-lived conducting state, then, given that one contact is well-defined (and long lived) via the RGD-protein interaction, the weak link would be the nonspecifically bonded contact at the second electrode. A 'weak link' that dominates the system conductance might qualitatively account for the correlation between peak current and "on" time (FIGS. 18B, 18C). The matrix element connecting two sites A, B can be written in terms of the tunneling currents between all the intervening atoms according to the tunneling flux theorem:

$$V_{AB} = -\hbar \Sigma_{\text{all coupled states}} J_{ab} \quad (4)$$

where $J_{ab}$ is the tunnel current operator evaluated between all intervening atomic sites. Tunnel current increases with the magnitude of the matrix element that connects the sites, or, in the simplest possible case, $V_{AB} = fi$ where f is a scale factor (that could presumably be calculated using eqn. 4, given a structure). If $V_{AB}$ also describes the bond strength coupling sites A and B, then the bond lifetime would be given by $$t \propto \exp\left(\frac{\Delta E}{kT}\right) \propto e^{fi/kT}.$$

Thus, the logarithmic dependence of current on bond lifetimes (FIGS. 18C and 18D) may reflect a direct correspondence between the matrix element for tunneling and the bonding energy of the link that dominates conductance.

Figure 20:
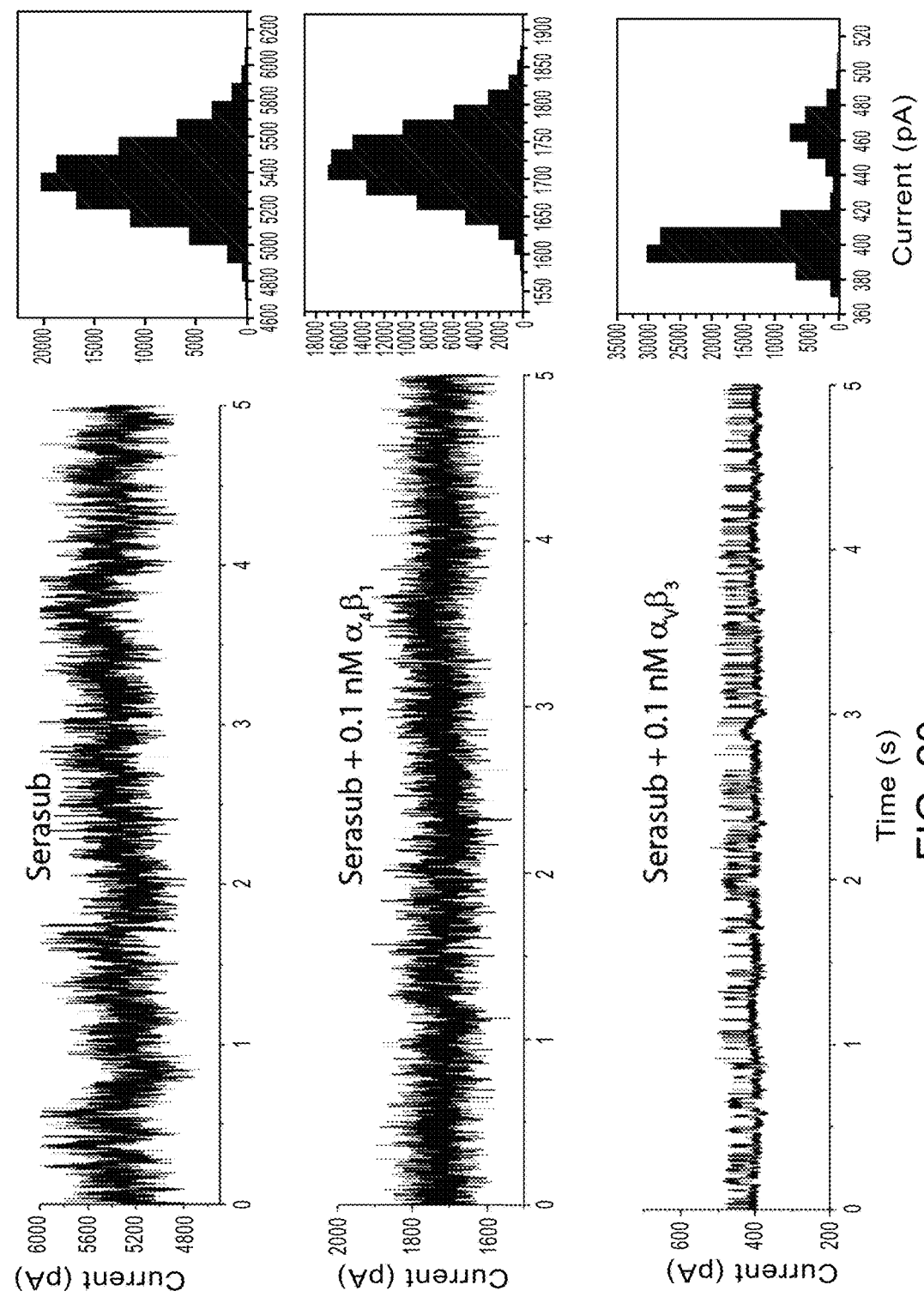
FIG. 20 is a series of graphs showing detection of a target protein in Serasub, a human serum that is protein free. The top trace is taken in undiluted Serasub, used as received, at a tunneling bias of 200 mV. The middle trace is 0.1 nM $\alpha_4\beta_1$ added to the undiluted Serasub. The background current has fallen considerably, possibly reflecting scavenging of electroactive components from the solution. The current continued to fall with time, so that when 0.1 nM $\alpha_V\beta_3$ was added 2LS signals were observed. In general, binding os a target molecule is indicated by a change in shape of the amplitude distribution after an analyte is introduced to the solution that did not previously contain the analyte.

Potential as a single molecule detector: The appearance of 2LS noise is a distinctive feature of specific binding and might therefore signal the detection of a target molecule even in a noisy environment, such as that which may be found in human serum, for example. As a first step in exploring this, we tested a device in Serasub (CST Technologies, Great Neck, N.Y.), a protein-free serum substitute (FIG. 20). In the undiluted serum, leakage currents were very high (5 nA initially, falling continuously with time) but the noise distribution in the presence of 0.1 nM $\alpha_v\beta_3$ was strikingly different from that in the serum alone, or serum plus $\alpha_1\beta_4$ where the appearance of 2LS is quite clear. Thus, the conductance fluctuations described here might be exploited for the development of a label-free single-molecule electronic detection system that could function in a noisy environment. In FIG. 20, the noise in the presence of serum alone is distributed in a Gaussian manner. The binding of a single recognized molecule adds a feature to the noise that contains predominantly two signal levels, one centered on the original mean noise level and the other resulting in a distinct additional feature in the amplitude distribution as shown in the bottom panel of FIG. 20. In the most general embodiment, a noise distribution would be measured in the absence of analyte and characterized, usually by fitting a Gaussian function to it. Data are subsequently recorded in the presence of the analyte and the shape of the noise distribution compared to that taken before the analyte was introduced. Binding of a recognized-molecule is indicated by a change in shape of this amplitude distribution.

Thus, an electrochemically-inert protein can be driven into a highly conducting state via the application of a small bias in a nano-junction device. This effect requires specific chemical attachment to one electrode in a fixed-gap device, offering a path to single molecule detection. The magnitude of the conductance fluctuations is completely unexpected, and without a known explanation, though the argument that proteins may exist in a quantum-critical state cannot be dismissed.

Methods

Functionalizing STM probes and substrates: The STM probes were etched from a 0.25 mm Pd wire (California Fine Wires) by an AC electrochemical etching method, and then insulated with high-density polyethylene, leaving an open apex of a few tens of nanometers in diameter. Before use, the probes were tested in 1 mM phosphate buffer (pH=7.4) at 0.5 V bias to ensure that the leakage current was <1 pA. For functionalization, the probe was gently cleaned using ethanol and water, respectively, and then dried with nitrogen flow. The probe was immersed in a 0.5 mg/mL peptide solution for ~20 h. After that, the probe was taken out, rinsed with water, dried with nitrogen gas, and used immediately. Palladium substrates were prepared by depositing a 100 nm palladium film onto a 10 nm titanium adhesion layer coated onto a 750 μm thick silicon wafer using an electron-beam evaporator (Lesker PVD 75). The substrate was annealed with a hydrogen flame immediately before being functionalized by the same method as that for probe. Fourier transform infrared (FTIR) spectroscopy was used to characterize the functionalization. Pd substrates were also treated by UV- Ozone cleaner and $H_2$ gas reduction (to remove PdO).

Preparation of RGD and RGE: RGD peptide, cyclo(Arg-Gly-Asp-D-Phe-Cys), was obtained from Peptides International (Louisville, Ky.). RGE peptide, cyclo(Arg-Gly-Glu-D-Phe-Cys), was synthesized by CPC Scientific (Sunnyvale, Calif.) with a purity>95%. For chip and STM tip functionalization, peptides were dissolved to a final concentration of 0.5 mg/mL in a freshly degassed 1 mM phosphate buffer (pH=7.4), which was prepared using water from a Milli-Q system with a resistance of ~18 MΩ and a total organic carbon contamination below 4 ppb.

Reference electrodes: Ag/AgCl wires were prepared by soaking Ag wires in chloride bleach for at least 4 hours. The electrode was then housed in a pipette tip, using 3 M KCl as the electrolyte and 5% agarose gel as the plug. As there are some KCl leakage from the gel plug into the STM cell (which can increase the tip leakage current) the KCl concentration was reduced to 10 mM for STM measurements. This resulted in a shift of about 100 mV in reference potential, and it has been accounted for in references to $V_r$.

Cyclic voltammetry: Cyclic voltammetry was performed on a potentiostat (Model AFCBP1, Pine Instruments), with a Pt wire counter electrode, a salt-bridged Ag/AgCl reference electrode (3 M KCl), and a sweep rate of 5 my/s. The area of Pd electrode was 0.5 cm×1 cm. Successive sweeps are increased by ±50 mV.

STM Measurements: Break junction measurements were carried out with a PicoSPM scanning probe microscope (Agilent Technologies). The Teflon liquid cells were cleaned in Piranha solution and then sonicated in Milli-Q water three times (Note that: the Piranha is highly corrosive and must be handled with extreme care). The current set point was 4 pA. Different sample bias was applied to the substrate as required. For better surface charge control, an Ag/AgCl with a salt bridge (10 mM KCl) was connected to the substrate. The tip was approached to the substrate with an integral and proportional gain of 1.0 and then left to stabilize for 0.5 h. For break junction measurements, the tip was first brought into the set point position. After 5 s of waiting, the tip was retracted 10 nm from the substrate with a speed of 0.17 nm/s, during which a current-distance trace was recorded. Subsequently, the tip was re-engaged and the retraction process repeated. About one hundred traces were collected for each experiment and at least three independent experiments were conducted for each sample (using a different substrate and tip each time).

Fabrication of devices: Devices were fabricated on 25 nm thick suspended SiN membranes supported on 0.2 mm thick silicon wafers above 10 μm square openings. 10 nm thick Pd electrodes were deposited using electron beam evaporation, followed by lift off to define an electrode width of 20 μm in the active region of the device, with connections made to gold contact pads at the side of the device. Eight devices were fabricated on a single one-inch wafer, and the assembly was then coated with a 4.8 nm thick layer of $Al_2O_3$ using 22 cycles of atomic layer deposition. The fabrication steps up to this point were carried out by Norcada Inc. (Edmonton, Alberta) for the most recent devices. Top electrodes are placed over the ALD using a further 10 nm deposition of Pd followed by e-beam lithography to form nanowires of between 80 and 100 nm width as top electrodes. The ALD has a high density of pinholes, but these are generally avoided when narrow wires are used Finally PECVD or ALD was used to cover the entire device with 20 nm of $SiO_2$. These latter steps were carried out in the Nanofabrication facility at ASU.

RIE Etching of devices: The SiN membranes were first thinned from below using a PlasmaTherm 790 RIE with $CF_4$ (50 sccm) and Ar (1 sccm) at 200W and 30 mT pressure for about 20 seconds, reducing the support membrane to 10 to 15 nm in thickness. 10 nm of Cr hard mask were grown thermally on the top of the $SiO_2$ passivation and either 80 nm of PMMA resist or 350 nm of ZEP520A spun on top of the Cr layer. The resist was patterned by EBL to expose the Cr hard mask. The Cr hard mask was then opened by wet etching with Cyantek CR7s for 22 to 26 s.

The underlying $SiO_2$ was opened by Floey RIE ($CHF_3$, 25 sccm, Ar, 25 sccm) using 200 W at a pressure of 30 mT for 90 s. The top Pd electrode was opened using a Plasma-Therm 790 RIE ($CHF_3$ 20 sccm, Ar 30 sccm and $O_2$ 5 sccm) at a power of 200 W and a pressure of 20 mT for times between 160 and 180 s. The $Al_2O_3$ dielectric was opened using Cloey RIE ($BCl_3$ 40 sccm) at 200 W and a pressure of 15 mT for 55 to 60 s. The bottom Pd electrode was then etched in the Plasma-Therm RIE as described above, followed finally by Plasma-Therm RIE of the SiN support membrane ($CF_4$ 50 sccm, Ar 1 sccm) using 200 W at a pressure of 30 mT for 240 to 300 s). The remaining Cr hard mask was removed using an Apex ICP-RIE ($O_2$ 8 sccm, $Cl_2$ 32 sccm, pressure=10 mT, Coil RF=800 W, Platen RF=20 W, exposure time 8 s).

Characterization of device openings: Devices were imaged using a JEOL 2010 TEM in the HREM facility at ASU. Cross sections were cut using an FEI Novascan 200 Ga ion FIB. These were generally 100 nm thick and embedded in Pt/C.

Sample Preparation and Electrical Measurements: Chips were tested at each step to make sure no current could be measured across the tunnel junction (the Simmons formula showing that currents should be negligible). Three top electrodes for each device were originally connect in a T (see FIG. 16C) so that they could be tested for continuity prior to etching the openings. After formation of the openings, chips were cleaned using a UV-Ozone cleaner (Novascan) for 20 minutes on each side to remove organic contamination, followed by reduction of oxidized Pd in a flow of H2 gas at 80° C. Chips were then soaked in 0.5 mg/mL RGD solution in 1 mM phosphate buffer (PB, pH=7.4) for 20 h. After that, chips were rinsed with water, blown dry with $N_2$ gas and mounted in a custom cell with an integrated contact set for the tunnel junctions. An Ag/AgCl reference electrode coupled by a salt bridge was mounted in the sample chamber. The chamber was filled with 1 mM phosphate buffer (PB, pH=7.4) and tested for leakage and to ensure that no spurious signals were being generated. Substantial (constant, dc) leakage was often measured at this point and it has been traced to a high density of pinholes in both the glass passivation layer and the alumina dielectric layer, often increasing with prolonged use of the device. However, no 2LS signals were observed. Integrin $\alpha 4\beta 1$ was purchased from R&D Systems (Bio-Techne), and $\alpha V\beta 3$ from YO Proteins AB. 100 nM integrin solutions were prepared using 1 mM PB and diluted into lower concentrations. The tunnel junction was biased using the voltage clamped output of an Axopatch 200B and current recorded using the Axopatch interface (Digidata 1550). The reference electrode was biased using a small, adjustable floating supply. The data acquisition rate was 100 kHz and the data were filtered with a 10 kHz low pass filter.

Electronic Structure Calculations: The exact numerical solution of the Schrödinger equation for the electronic states of large molecules such as proteins is a prohibitive task. Various approximations have been developed, which reduce the problem to a one-electron problem in the effective field of the remaining electrons. Wave functions of molecules are usually written in the form of Linear Combinations of Atomic Orbitals (LCAO) $\phi_i = \Sigma_r C_{i,r} \chi_r$, where $\phi_i$ is a Molecular Orbital (MO) represented as the sum of atomic orbital (AO) contributions $\chi_r$. The one-electron eigenenergies and eigenvectors then can be determined from the generalized eigenvalue equation HC=ESC, where $S_{rs} = \langle \chi_r | \chi_s \rangle$ and $H_{rs} = \langle \chi_r | H_{eff} | \chi_s \rangle$ are the overlap and effective Hamiltonian matrices respectively. The effective Hamiltonian depends on the coefficients, which makes the problem nonlinear in C. This is the case in Hartree-Fock and Density Functional Theory (DFT) calculations, which then cannot be routinely carried out for proteins involving thousands of atoms. If interest is restricted to the localization-delocalization problem in valence electrons and treat the two-electron part of the Hamiltonian as in the case of the electrons in metals, in an average sense only, semi-empirical methods can be applied. Once the positions of the atoms are known the Extended Hückel (EH) Molecular Orbital Method is quite successful in calculating the MOs of organic molecules. The diagonal part $H_{rr}^{(EH)}$ of the EH Hamiltonian is given by the ionization energies of the AOs, while the off-diagonal elements are calculated from the diagonal elements and the overlap matrix $H_{rs}^{EH} = \frac{1}{2} K (H_{TT}^{EH} + H_{SS}^{EH}) S_{rs}$ where the common choice for the empirical constant is K=1.75. This is similar in spirit to other tight binding Hamiltonians in solid state physics. For the numerical studies, X-ray diffraction data of $\alpha_r\beta_3$ Integrin from the Protein Data Bank of RCSB was selected. It consists of 959 amino acids and weighs about 190690.25 Daltons (no water molecules). The Open Babel tool (The Open Babel Package, version 2.3.2 openbabel.org accessed April 2016) has been used to add hydrogen atoms to the X-ray diffraction structure (PDB ID: 4G1M). The EH calculations have been carried out by the numerical package YAeHMOP (yaehmop.sourceforge.net/, accessed April 2016). There are N=65322 valence electron AOs and the EH Hamiltonian and overlap matrices are of dimension 65322×65322. The source code of YAeHMOP has been modified from 32 bit operations to 64 bit operations to accommodate such large matrices. The energy levels computed with the EH method have been analyzed with a statistical method of R., V., *Fluctuations in level spectra-role of range*. J. Phys., 1982. B15: p. 4293. First, a number of degenerate energy levels have been removed from the spectrum. These degenerate levels do not belong to the spectrum of the protein, instead they come from many isolated identical molecules (such as $H_2O$) which do not interact with the protein, and are just artifacts in the structure file. After this procedure N=55837 energy levels remained.

The distance between consecutive energy levels fluctuates in the spectrum. The raw distance between levels $\sigma_n = E_{n+1} - E_n$ can be normalized using the mean energy level distance $\Delta(E)$ at a given energy window around E. The ratio $s_n = \sigma_n / \Delta(E_n)$ is called the level spacing. The mean energy level distance is calculated as the average of k level spacings to the left and to the right $$\Delta(E_n) = \frac{1}{2k+1} \sum_{j=-k}^{+k} \sigma_{n+j}.$$

The choice of k depends on the variability of the density of energy levels. Statistical averaging would require large values, while fast variation (especially singularities) in the density of energy levels restricts our choice to low values. It was found that a choice of k=2 ensures the stability of the distribution in our examples. Next, following standard procedures, the cumulative spacing $1(s) = \int_0^s P(s)ds$ is calculated and compared to the theoretical predictions. For the Poissonian statistics (Eqn. 2) $I_p(s) = 1 - e^{-s}$, for the Wigner surmise (Eqn. 1) $I_W(s) = 1 - e^{-\pi s^2/4}$ and for the semi-Poissonian transitional statistics (Eqn. 3) $I_T(s) = 1 - (2s+1)e^{-2s}$. In FIG. 6. it is shown the cumulative level spacing and in the inset, it is shown the difference of the calculated to the theoretical $I_T(s)$. Without any parameter fitting, the spacings for $\alpha_V\beta_3$ Integrin follow the critical theoretical curve with astonishing precision. Note, that no parameter fitting is involved in the procedure, the calculated spacing distribution has a less than 4% error like in the case of systems of critical quantum chaos, which are purely theoretical models as opposed to our case, where the positions of atoms in the protein are obtained experimentally. It should be emphasized again, that finding a large tight binding Hamiltonian tuned exactly or almost exactly to the critical point by random chance can happen only with an astronomically low probability. So, finding just a single protein with about 1000 amino acids having this property at random is impossible.

Any and all references to publications or other documents, including but not limited to, patents, patent applications, articles, webpages, books, etc., presented anywhere in the present application, are herein incorporated by reference in their entirety.

As noted elsewhere, the disclosed embodiments have been presented for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, compositions, systems and apparatuses/devices which may further include any and all elements from any other disclosed methods, compositions, systems, and devices, including any and all elements corresponding to detecting one or more target molecules (e.g., DNA, proteins, and/or components thereof). In other words, elements from one or another disclosed embodiments may be interchangeable with elements from other disclosed embodiments. Moreover, some further embodiments may be realized by combining one and/or another feature disclosed herein with methods, compositions, systems and devices, and one or more features thereof, disclosed in materials incorporated by reference. In addition, one or more features/elements of disclosed embodiments may be removed and still result in patentable subject matter (and thus, resulting in yet more embodiments of the subject disclosure). Furthermore, some embodiments correspond to methods, compositions, systems, and devices which specifically lack one and/or another element, structure, and/or steps (as applicable), as compared to teachings of the prior art, and therefore represent patentable subject matter and are distinguishable therefrom (i.e. claims directed to such embodiments may contain negative limitations to note the lack of one or more features prior art teachings).

Also, while some of the embodiments disclosed are directed to detection of a protein molecule, within the scope of some of the embodiments of the disclosure is the ability to detect other types of molecules.

When describing the molecular detecting methods, systems and devices, terms such as linked, bound, connect, attach, interact, and so forth should be understood as referring to linkages that result in the joining of the elements being referred to, whether such joining is permanent or potentially reversible. These terms should not be read as requiring a specific bond type except as expressly stated.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

LITERATURE CITED

DEVICES AND METHODS FOR TARGET MOLECULE CHARACTERIZATION. US Aplication 2010/0084276 A1
DIGITAL PROTEIN SENSING CHIP AND METHODS FOR DETECTION OF LOW CONCENTRATIONS OF MOLECULES Application 61/980,317 filed Apr. 16 2014
METHODS AND APPARATUSES AND SYSTEMS FOR STABILIZING NANO-ELECTRIC DEVICES IN CONTACT WITH SOLUTIONS application 61/944,322.
Artes, J. M., I. Diez-Perez and P. Gorostiza (2012). "Transistor-like behavior of single metalloprotein junctions." *Nano Lett* 12(6): 2679-2684.
Choi, Y., E. Kim, Y. Lee, M. H. Han and I. C. Kang (2010). "Site-specific inhibition of integrin alpha v beta 3-vitronectin association by a ser-asp-val sequence through an Arg-Gly-Asp-binding site of the integrin." *Proteomics* 10(1): 72-80.
Cui, X. D., A. Primak, X. Zarate, J. Tomfohr, O. F. Sankey, A. L. Moore, T. A. Moore, D. Gust, G. Harris and S. M. Lindsay (2001). "Reproducible measurement of single-molecule conductivity." *Science* 294: 571-574.
Pang, P., B. Ashcroft, W. Song, P. Zhang, S. Biswas, Q. Qing, J. Yang, R. J. Nemanich, J. Bai, J. Smith, K. Reuter, V. S. K. Balagurusamy, Y. Astier4, G. Stolovitzky and S. Lindsay (2014). "Fixed Gap Tunnel Junction for Reading DNA Nucleotides." *ACS Nano* 8: 11994-12003.
Pishrody, S. M., S. Kunwar and G. T. Mathai (2004). Electronic Detection of Biological Molcules using thin layers, U.S. Pat. No. 6,824,974 B2 Nov. 30 2004.
Ulstrup, J. (1979). *Charge transfer processes in condensed media*. Berlin, Springer-Verlag.
Vattay, G., D. Salahub, I. Csabai, A. Nassimi and S. A. Kaufmann (2015). "Quantum Criticality at the Origin of Life." *arXiv:*1502.06880 [*cond-mat.dis-nn*].
Xiao, X., B. Xu and N. Tao (2004). "Conductance Titration of Single-Peptide Molecules." *J. Am Chem Soc* 126: 5370-5371.
Zwolak, M. and M. Di Ventra (2005). "Electronic Signature of DNA Nucleotides via Transverse Transport." *Nano Lett*. 5: 421-424.
Nitzan, A., *Chemical dynamics in condensed phases*. 2006, Oxford: Oxford University Press.
Onuchic, J. N., et al., *Pathway analysis of protein electron-transfer reactions*. Annu Rev Biophys Biomol Struct, 1992. 21: p. 349-77.
Polizzi, N. F., S. S. Skourtis, and D. N. Beratan, *Physical Constraints on Charge Transport through Bacterial Nanowires*. Faraday Discussions, 2012. 153: p. 43-62.
Beratan, D. N., et al., *Charge transfer in dynamical biosystems, or the treachery of (static) images*. Acc Chem Res, 2015. 48(2): p. 474-81.
Artes, J. M., et al., *Conductance switching in single wired redox proteins*. Small, 2014. 10(13): p. 2537-41.
Kumar, K. S., et al., *Long-Range Tunneling Processes across Ferritin-Based Junctions*. Adv Mater, 2016. 28(9): p. 1824-30.
Malvankar, N. S., et al., *Tunable metallic-like conductivity in microbial nanowire networks*. Nat Nanotechnol, 2011. 6(9): p. 573-9.
Amdursky, N., et al., *Electronic transport via proteins*. Adv Mater, 2014.26(42): p. 7142-61.
Thomson, N. H., et al., *Molecular images of cereal proteins by STM*. Ultramicroscopy, 1992. 42-44 (Pt B): p. 1204-13.
Bertazzon, A., B. M. Conti-Tronconi, and M. A. Raftery, *Scanning tunneling microscopy imaging of Torpedo acetylcholine receptor*. Proc Natl Acad Sci USA, 1992. 89(20): p. 9632-6.
Leatherbarrow, R. J., M. Stedman, and T. N. Wells, *Structure of immunoglobulin G by scanning tunnelling microscopy*. J Mol Biol, 1991. 221(2): p. 361-5.
Xiong, J. P., et al., *Crystal structure of the extracellular segment of integrin alpha Vbeta3 in complex with an Arg-Gly-Asp ligand*. Science, 2002. 296(5565): p. 151-5.
Sancey, L., et al., *Clustering and internalization of integrin alphavbeta3 with a tetrameric RGD-synthetic peptide*. Mol Ther, 2009. 17(5): p. 837-43.
Palecek, E., et al., *Electrochemistry of nonconjugated proteins and glycoproteins. Toward sensors for biomedicine and glycomics*. Chem Rev, 2015. 115(5): p. 2045-108.
Luo, B. H., C. V. Carman, and T. A. Springer, *Structural basis of integrin regulation and signaling*. Annu Rev Immunol, 2007. 25: p. 619-47.
Pang, P., et al., *Fixed-Gap Tunnel Junction for Reading DNA Nucleotides*. ACS nano, 2014. 8(12): p. 11994-12003.
Engel, G. S., et al., *Evidence for wavelike energy transfer through quantum coherence in photosynthetic systems*. Nature, 2007. 446(7137): p. 782-6.
Lloyd, S., *Quantum coherence in biological systems*. Journal of Physics: Conference Series, 2011. 302: p. 012037.
Vattay, G., et al., *Quantum criticality at the origin of life*. Journal of Physics: Conference Series, 2015. 626: p. 012023.
Im, J., et al., *Electronic single-molecule identification of carbohydrate isomers by recognition tunnelling*. Nat Commun, 2016. 7: p. 13868.
Chang, S., et al., *Palladium electrodes for molecular tunnel junctions*. Nanotechnology, 2012. 23(42): p. 425202.
Grdeń, M., et al., *Electrochemical behaviour of palladium electrode: Oxidation, electrodissolution and ionic adsorption*. Electrochimca Acta, 2008. 53: p. 7583-7806.

Chang, S., et al., *Gap distance and interactions in a molecular tunnel junction.* J Am Chem Soc, 2011. 133(36): p. 14267-9.
Pang, P., et al., *Fixed-gap tunnel junction for reading DNA nucleotides.* ACS Nano, 2014. 8(12): p. 11994-2003.
Arielly, R., et al., *Real-time detection of redox events in molecular junctions.* J Am Chem Soc, 2014. 136(6): p. 2674-80.
Zhang, Y., et al., *Biological charge transfer via flickering resonance.* Proc Natl Acad Sci USA, 2014. 111(28): p. 10049-54.
Fan, F. R. F. and A. J. Bard, *Electrochemical detection of single molecules.* Science, 1995. 267: p. 871-874.
Carslaw, H. S. and J. C. Jaeger, *Conduction of Heat in Solids.* 1959: Oxford University Press.
Haiss, W., vanZalinge, H., Bethell, D., Ulstrup, J., Schiffrin, D. J., Nichols, R. J., *Thermal gating of the single molecule conductance of alkanedithiols.* Faraday Discussions, 2006. 131: p. 253.
Lindsay, S., et al., *Recognition tunneling. Nanotechnology,* 2010. 21(26): p. 262001.
Stuchebrukhov, A. A., *Towards ab initio theory of long-distance electron tunneling in proteins: Tunneling Currents Approach.* Adv. Chem. Phys. , 2001. 118: p. 1-44.
Simmons, J. G., *Generalized formula for the electric tunnel effect between similar electrodes separated by a thin insulating film.* J. Appl. Phys., 1963. 34(6): p. 1793-1803.
Hoffmann, R., *An extended Hückel theory. I. hydrocarbons.* J. Chem. Phys., 1963. 39: p. 1397-1412.
Dong, X., et al., *alpha(V)beta(3) integrin crystal structures and their functional implications.* Biochemistry, 2012. 51(44): p. 8814-28.
O'Boyle, N. M., et al., *Open Babel: An open chemical toolbox.* J Cheminform, 2011. 3: p. 33.
E. B., B., G. U., and S. C., *Models of intermediate spectral statistics.* Phys. Rev .E, 1999. 59: p. R1315.
E., B. and S. C., *Structure of wave functions of pseudointegrable billiards.* Phys. Rev. Lett. , 2004. 92: p. 244102.

What is claimed is:

1. A sensing device comprising:
a first electrode; and
a second electrode separated from the first electrode by a gap,
wherein:
the first electrode and the second electrode include an opening formed therethrough,
at least one of the first electrode and the second electrode is functionalized with at least one recognition molecule,
the recognition molecule has an effective length L1 and is configured to selectively bind to a target molecule having an effective length L2, and
the size of the gap is configured to be greater than 2L1, but less than or equal to the sum of 2L1 and L2, so that the gap is bridged by the target molecule bound by the at least one recognition molecule, thereby completing an electrical circuit.

2. A method for detecting a target molecule in a sensing device, the method comprising:
recording a first current over time when a solution suspected of having the target molecule is in contact with the sensing device, wherein
the sensing device includes a first electrode and a second electrode separated from the first electrode by a gap,
the first electrode and the second electrode including an opening formed therethrough,
at least one of the first electrode and the second electrode is functionalized with a recognition molecule,
the recognition molecule having an effective length L1 and configured to selectively bind to the target molecule having an effective length L2, and
the size of the gap is configured to be greater than 2L1, but less than or equal to the sum of 2L1 and L2;
obtaining a distribution of amplitudes of the first current;
comparing the distribution of amplitudes with a reference distribution, wherein the reference distribution is obtained by recording a second current over time when a test solution is in contact with the sensing device, and the test solution is substantially free of the target molecule; and
determining that the target molecule is detected if the distribution of amplitudes is substantially different from the reference distribution in shape.

3. The method of claim 2, further comprising obtaining a mean baseline value for the second current recorded over time.

4. The method of claim 3, wherein the target molecule is detected when the distribution of amplitudes of the first current includes features of a constant current height above the mean baseline value for the second current recorded over time.

5. The method of claim 2, wherein the distribution of amplitudes or the reference distribution is obtained by sampling amplitudes at a time interval of about 0.01 microseconds to 1 second.

6. The method of claim 4, wherein the constant current height is about 1 picoamp to 1 microamp.

7. The method of claim 2, wherein the distribution of amplitudes cannot be fitted by a single Gaussian.

8. The method of claim 2, wherein the reference distribution can be fitted by a single Gaussian.

9. The method of claim 2, wherein the distribution of amplitudes is substantially different from the reference distribution when the distribution of amplitudes cannot be fitted by a single Gaussian and the reference distribution can be fitted by a single Gaussian.

10. The method of claim 2, wherein the target molecule is a protein, DNA, or RNA.

11. A method for detecting a target molecule in a sensing device, the method comprising:
recording a first distribution of current signals when a test solution substantially free of the target molecule is in contact with the sensing device, wherein
the sensing device includes a first electrode and a second electrode separated from the first electrode by a gap,
the first electrode and the second electrode including an opening formed therethrough,
at least one of the first electrode and the second electrode is functionalized with a recognition molecule,
the recognition molecule having an effective length L1 and configured to selectively bind to the target molecule having an effective length L2, and
the size of the gap is configured to be greater than 2L1, but less than or equal to the sum of 2L1 and L2;
contacting a sample solution suspected of having the target molecule with the sensing device;
recording a second distribution of current signals when the sample solution is in contact with the sensing device, and determining that the target molecule is present in the sample solution when the second distribution has a different shape as compared to the first distribution.

12. The method of claim 11, wherein the first distribution can be fitted by a single Gaussian.

13. The method of claim 11, wherein the second distribution cannot be fitted by a single Gaussian.

14. The method of claim 11, wherein the target molecule is a protein, DNA, or RNA.

* * * * *

UNITED STATES PATENT AND TRADEMARK OFFICE
CERTIFICATE OF CORRECTION

PATENT NO. : 10,422,787 B2  
APPLICATION NO. : 15/797052  
DATED : September 24, 2019  
INVENTOR(S) : Stuart Lindsay, Peiming Zhang and Yanan Zhao Page 1 of 1

It is certified that error appears in the above-identified patent and that said Letters Patent is hereby corrected as shown below:

In the Specification

Please replace the paragraph under the header "Government Rights" with the following paragraph: "This invention was made with government support under R01 HG006323, R01 HG009180 awarded by The National Institutes of Health. The government has certain rights in the invention."

Signed and Sealed this  
Twelfth Day of November, 2019

Andrei Iancu  
*Director of the United States Patent and Trademark Office*